(12) United States Patent
Gunderson

(10) Patent No.: US 9,037,240 B2
(45) Date of Patent: May 19, 2015

(54) ELECTRODE LEAD INTEGRITY REPORTS

(75) Inventor: Bruce D. Gunderson, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 1324 days.

(21) Appl. No.: 12/180,314

(22) Filed: Jul. 25, 2008

(65) Prior Publication Data

US 2009/0299201 A1    Dec. 3, 2009

Related U.S. Application Data

(60) Provisional application No. 61/058,150, filed on Jun. 2, 2008.

(51) Int. Cl.
| A61N 1/36 | (2006.01) |
| A61N 1/372 | (2006.01) |
| A61N 1/362 | (2006.01) |
| A61N 1/37 | (2006.01) |
| A61N 1/39 | (2006.01) |
| A61N 1/08 | (2006.01) |

(52) U.S. Cl.
CPC .......... *A61N 1/37247* (2013.01); *A61N 1/3621* (2013.01); *A61N 1/3704* (2013.01); *A61N 1/3925* (2013.01); *A61N 2001/083* (2013.01)

(58) Field of Classification Search
CPC .............................................. A61N 2001/083
USPC ..................................... 607/27, 28
See application file for complete search history.

(56) References Cited

U.S. PATENT DOCUMENTS

| 4,140,131 A | 2/1979 | Dutcher et al. |
| 4,374,382 A | 2/1983 | Markowitz |
| 4,428,378 A | 1/1984 | Anderson et al. |
| 4,549,548 A | 10/1985 | Wittkampf et al. |
| 4,825,869 A | 5/1989 | Sasmor et al. |

(Continued)

FOREIGN PATENT DOCUMENTS

| EP | 1857141 A1 | 11/2007 |
| WO | WO02/18009 A1 | 3/2002 |
| WO | WO2005/056109 A1 | 6/2005 |

OTHER PUBLICATIONS

International Preliminary Report on Patentability for PCT/US2008/009079 dated Dec. 16, 2010, (7 pp.)

(Continued)

*Primary Examiner* — Eric D. Bertram
(74) *Attorney, Agent, or Firm* — Michael J. Ostrom

(57) ABSTRACT

In general, the disclosure relates to techniques for providing a combination of stored diagnostic information, including impedance trend data, into one displayable report that may be used to diagnose a possible condition with an implantable medical electrode lead. One example device includes a processor that is configured to obtain impedance trend data for an electrical path, the electrical path comprising a plurality of electrodes, and to obtain additional diagnostic data that is associated with the electrical path, the additional diagnostic data being distinct from the impedance trend data. The device is further configured to combine both the impedance trend data and the additional diagnostic data into a displayable report that indicates whether there is a possible condition with the electrical path. The additional diagnostic data may include non-sustained episode data, sensing integrity data, pacing threshold, and/or electrogram data (such as P-wave amplitude and/or R-wave amplitude data).

45 Claims, 16 Drawing Sheets

(56) References Cited

U.S. PATENT DOCUMENTS

| | | |
|---|---|---|
| 4,860,749 A | 8/1989 | Lehmann |
| 4,899,750 A | 2/1990 | Ekwall |
| 4,913,146 A | 4/1990 | DeCote, Jr. |
| 4,944,746 A | 7/1990 | Iwata et al. |
| 5,003,975 A | 4/1991 | Hafelfinger et al. |
| 5,107,833 A | 4/1992 | Barsness |
| 5,117,824 A | 6/1992 | Keimel et al. |
| 5,137,021 A | 8/1992 | Wayne et al. |
| 5,168,871 A | 12/1992 | Grevious |
| 5,184,614 A | 2/1993 | Collins et al. |
| 5,193,535 A | 3/1993 | Bardy et al. |
| 5,201,865 A | 4/1993 | Kuehn |
| 5,215,081 A | 6/1993 | Ostroff |
| 5,224,475 A | 7/1993 | Berg et al. |
| 5,226,415 A | 7/1993 | Girodo et al. |
| 5,292,343 A | 3/1994 | Blanchette et al. |
| 5,312,441 A | 5/1994 | Mader et al. |
| 5,314,450 A | 5/1994 | Thompson |
| 5,324,315 A | 6/1994 | Grevious |
| 5,354,319 A | 10/1994 | Wyborny et al. |
| 5,381,803 A | 1/1995 | Herleikson et al. |
| 5,383,909 A | 1/1995 | Keimel |
| 5,411,530 A | 5/1995 | Akhtar |
| 5,431,692 A | 7/1995 | Hansen et al. |
| 5,462,060 A | 10/1995 | Jacobson et al. |
| 5,507,746 A | 4/1996 | Lin |
| 5,507,786 A | 4/1996 | Morgan et al. |
| 5,534,018 A | 7/1996 | Wahlstrand et al. |
| 5,545,183 A | 8/1996 | Altman |
| 5,545,186 A | 8/1996 | Olson et al. |
| 5,549,646 A | 8/1996 | Katz et al. |
| 5,558,098 A | 9/1996 | Fain |
| 5,564,434 A | 10/1996 | Halperin et al. |
| 5,660,183 A | 8/1997 | Chiang et al. |
| 5,707,398 A | 1/1998 | Lu |
| 5,722,997 A | 3/1998 | Nedungadi et al. |
| 5,730,141 A | 3/1998 | Fain et al. |
| 5,741,311 A | 4/1998 | McVenes et al. |
| 5,749,907 A | 5/1998 | Mann |
| 5,755,735 A | 5/1998 | Richter et al. |
| 5,755,736 A | 5/1998 | Gillberg et al. |
| 5,755,742 A | 5/1998 | Schuelke et al. |
| 5,776,168 A | 7/1998 | Gunderson |
| 5,814,088 A | 9/1998 | Paul et al. |
| 5,868,793 A | 2/1999 | Nitzsche et al. |
| 5,891,170 A | 4/1999 | Nitzsche et al. |
| 5,891,179 A | 4/1999 | Er et al. |
| 5,897,577 A | 4/1999 | Cinbis et al. |
| 5,910,156 A | 6/1999 | Cinbis et al. |
| 5,944,746 A | 8/1999 | Kroll |
| 6,067,473 A | 5/2000 | Greeninger et al. |
| 6,070,097 A | 5/2000 | Kreger et al. |
| 6,085,118 A | 7/2000 | Hirschberg et al. |
| 6,112,119 A | 8/2000 | Schuelke et al. |
| 6,129,746 A | 10/2000 | Levine et al. |
| 6,141,585 A | 10/2000 | Prutchi et al. |
| 6,155,267 A | 12/2000 | Nelson |
| 6,169,923 B1 | 1/2001 | Kroll |
| 6,266,554 B1 | 7/2001 | Hsu et al. |
| 6,317,632 B1 | 11/2001 | Krig et al. |
| 6,317,633 B1 | 11/2001 | Jorgenson et al. |
| 6,434,428 B1 | 8/2002 | Sloman et al. |
| 6,445,952 B1 | 9/2002 | Manrodt et al. |
| 6,477,417 B1 | 11/2002 | Levine |
| 6,493,586 B1 | 12/2002 | Stahmann et al. |
| 6,629,931 B1 | 10/2003 | Begemann et al. |
| 6,650,931 B1 | 11/2003 | McClure et al. |
| 6,658,294 B1 | 12/2003 | Zadeh et al. |
| 6,721,600 B2 | 4/2004 | Jorgenson et al. |
| 6,760,624 B2 | 7/2004 | Anderson et al. |
| 6,788,971 B1 | 9/2004 | Sloman et al. |
| 6,865,141 B2 | 3/2005 | Tada et al. |
| 7,047,083 B2 | 5/2006 | Gunderson et al. |
| 7,167,747 B2 | 1/2007 | Gunderson et al. |
| 7,236,828 B2 | 6/2007 | Casavant et al. |
| 7,266,409 B2 | 9/2007 | Gunderson |
| 7,289,851 B2 | 10/2007 | Gunderson et al. |
| 7,333,855 B2 | 2/2008 | Gunderson et al. |
| 7,369,893 B2 | 5/2008 | Gunderson |
| 7,539,540 B2 | 5/2009 | Gunderson et al. |
| 7,567,835 B2 | 7/2009 | Gunderson et al. |
| 7,567,840 B2 | 7/2009 | Armstrong |
| 7,899,535 B2 | 3/2011 | Bohn et al. |
| 2001/0031997 A1 | 10/2001 | Lee |
| 2001/0037366 A1 | 11/2001 | Webb et al. |
| 2002/0091333 A1 | 7/2002 | Hsu et al. |
| 2002/0116031 A1 | 8/2002 | Vonk |
| 2002/0118215 A1 | 8/2002 | Ball et al. |
| 2002/0120307 A1 | 8/2002 | Jorgenson et al. |
| 2003/0074026 A1 | 4/2003 | Thompson et al. |
| 2003/0204215 A1 | 10/2003 | Gunderson et al. |
| 2004/0015197 A1 | 1/2004 | Gunderson |
| 2004/0064161 A1 | 4/2004 | Gunderson et al. |
| 2004/0088018 A1 | 5/2004 | Sawchuk et al. |
| 2004/0106955 A1 | 6/2004 | Swerdlow et al. |
| 2004/0122487 A1 | 6/2004 | Hatlestad et al. |
| 2004/0186388 A1 | 9/2004 | Gerasimov |
| 2004/0220631 A1 | 11/2004 | Burnes et al. |
| 2004/0230233 A1 | 11/2004 | Gunderson et al. |
| 2004/0230242 A1 | 11/2004 | van Dam et al. |
| 2005/0137636 A1* | 6/2005 | Gunderson et al. ............. 607/27 |
| 2005/0154421 A1 | 7/2005 | Ousdigian |
| 2005/0159785 A1 | 7/2005 | Rueter |
| 2006/0074454 A1 | 4/2006 | Freeberg |
| 2006/0116733 A1 | 6/2006 | Gunderson |
| 2006/0116773 A1 | 6/2006 | Cooney, III et al. |
| 2006/0235476 A1 | 10/2006 | Gunderson et al. |
| 2007/0293903 A1 | 12/2007 | Bohn et al. |
| 2008/0082012 A1 | 4/2008 | Gunderson et al. |
| 2008/0161872 A1 | 7/2008 | Gunderson |
| 2008/0215110 A1 | 9/2008 | Gunderson |

OTHER PUBLICATIONS

Danilovic et al, "Pacing Impedance Variability in Tined Steroid Eluting Leads," vol. 21, No. 7, Jul. 1, 1998, pp. 1356-1363.

International Search Report and Written Opinion from corresponding PCT Application Serial No. PCT/US2008/009079, mailed Feb. 25, 2009 (11 pgs.).

Danilovic et al., "Pacing Impedance Variability in Tined Steroid Eluting Leads," Jul. 1, 1998, pp. 1356-1363, vol. 21, No. 7, Malden, MA, US.

Parsonett et al., "Detection of Early Renal Transplant Rejection by Minimally-Invasive Monitoring of Impedance Variability," Biosensors & Bioelectronics, Mar. 30, 2007, pp. 2749-2750, vol. 22, No. 11, Barking, GB.

Valimaki et al., "Spectral analysis of cerebral electric impedance variability and arterial blood pressure variability in neonates with intraventricular haemorrhage," Cardiorespiratory Research Unit, University of Turku, Finland, and Biomedical Engineering Centre, Early Human Development, Shannon, IR, Aug. 1, 1988, p. 288, vol. 17, No. 1.

U.S. Appl. No. 12/180,304, filed Jul. 25, 2008 entitled "Impedance Variability Analysis to Identify Lead-Related Conditions", by Stadler et al.

International Preliminary Report on Patentability for PCT Application No. PCT/US2008/009027, mail date Jul. 15, 2010 (16 pp).

Office Action from U.S. Appl. No. 12/180,304, dated Jan. 9, 2012, 20 pp.

Response to Final Office Action mailed Jul. 13, 2012 for U.S. Appl. No. 12/180,304, filed Sep. 12, 2012 (9 pages).

Amendment in response to Final Office Action mailed Jul. 13, 2012 for U.S. Appl. No. 12/180,304, filed Oct. 12, 2012 (27 pages).

Office Action from U.S. Appl. No. 12/180,304, dated Jul. 13, 2012, 21 pp.

Response to Office Action dated Jan. 9, 2012, from U.S. Appl. No. 12/180,304, filed Apr. 6, 2012, 30 pp.

Notice of Allowance from U.S. Appl. No. 12/180,304 dated Sep. 30, 2013, 11 pp.

* cited by examiner

NON-SUSTAINED EPISODE DATA

Non-Sustained Episodes
40% (20/50) NST with V.Cycle < 200 ms

| ID# | Date/Time | A. Cycle | V. Cycle | Duration | Reason |
|---|---|---|---|---|---|
| 91 | Aug 10 12:25:10 | 830 ms | 210 ms | 6 beats | Non-Sustained |
| 90 | Aug 10 12:22:09 | 810 ms | 200 ms | 8 beats | Non-Sustained |
| 89 | Aug 10 12:16:49 | 760 ms ✚ | 190 ms | 7 beats | Non-Sustained |
| 88 | Aug 10 12:03:24 | 910 ms | 200 ms | 5 beats | Non-Sustained |
| 87 | Aug 10 11:56:33 | 820 ms | 180 ms | 7 beats | Non-Sustained |
| 86 | Aug 10 11:54:49 | 830 ms | 200 ms | 6 beats | Non-Sustained |
| 85 | Aug 10 11:41:12 | 800 ms | 200 ms | 5 beats | Non-Sustained |
| 84 | Aug 10 10:59:09 | 690 ms | 150 ms | 6 beats | Non-Sustained |
| 83 | Aug 10 10:58:03 | 700 ms | 180 ms | 5 beats | Non-Sustained |
| 82 | Aug 10 10:46:13 | 800 ms | 160 ms | 5 beats | Non-Sustained |
| 81 | Aug 10 10:46:11 | 800 ms | 190 ms | 6 beats | Non-Sustained |

Most Recent NST with V. Cycle < 200 ms

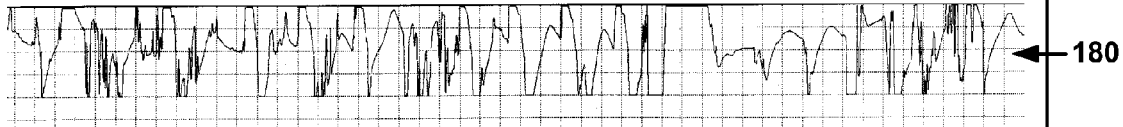

ELECTRODE LEAD INTEGRITY REPORTS

This application claims the benefit of U.S. Provisional Application No. 61/058,150, entitled "ELECTRODE LEAD INTEGRITY REPORTS" and filed on Jun. 2, 2008, the entire content of which is incorporated herein by reference.

TECHNICAL FIELD

This disclosure relates to implantable medical devices and associated devices, and, more particularly, to monitoring integrity of components associated with implantable medical devices.

BACKGROUND

A wide variety of implantable medical devices for delivering a therapy or monitoring a physiologic condition have been clinically implanted or proposed for clinical implantation in patients. Some implantable medical devices may employ one or more elongated electrical leads and/or sensors. Such implantable medical devices may deliver therapy and/or monitor the heart, muscle, nerve, brain, stomach or other organs. In some cases, implantable medical devices deliver electrical stimulation therapy and/or monitor physiological signals via one or more electrodes or sensor elements, which may be included as part of one or more elongated implantable medical leads. Implantable medical leads may be configured to allow electrodes or sensors to be positioned at desired locations for delivery of stimulation or sensing. For example, electrodes or sensors may be carried at a distal portion of the lead. A proximal portion of the lead that may be coupled to an implantable medical device housing, which may contain electronic circuitry such as stimulation generation and/or sensing circuitry.

For example, implantable medical devices, such as cardiac pacemakers or implantable cardioverter defibrillators, provide therapeutic stimulation to the heart by delivering electrical therapy signals such as pulses or shocks for pacing, cardioversion or defibrillation via electrodes of one or more implantable leads. In some cases, such an implantable medical device may sense intrinsic depolarizations of the heart, and control the delivery of such therapy signals to the heart based on the sensing. When an abnormal rhythm is detected, such as bradycardia, tachycardia or fibrillation, an appropriate electrical signal or signals may be delivered to restore or maintain a more normal rhythm. For example, in some cases, an implantable medical device may deliver pacing, cardioversion or defibrillation signals to the heart of the patient upon detecting ventricular tachycardia, and deliver cardioversion or defibrillation electrical signals to a patient's heart upon detecting ventricular fibrillation. Pacing signals typically have a lower energy than cardioversion or defibrillation signals.

Leads associated with such implantable medical devices typically include a lead body extending between a proximal lead end and a distal lead end. The lead body incorporates one or more exposed electrode or sensor elements located at or near the distal lead end. One or more elongated electrical conductors extend through the lead body from a connector assembly provided at a proximal lead end for connection with circuitry within an associated implantable medical device housing and an electrode located at the distal lead end or along a section of the lead body. Each electrical conductor is typically electrically isolated from other electrical conductors and is encased within an outer sheath that electrically insulates the lead conductors from body tissue and fluids.

Cardiac lead bodies tend to be continuously flexed by the beating of the heart. Other stresses may be applied to the lead body during implantation or lead repositioning. Patient movement can cause the route traversed by the lead body to be constricted or otherwise altered, causing stresses on the lead body. The electrical connection between implantable medical device connector elements and the lead connector elements can be intermittently or continuously altered. In some cases, changes in leads or connections may result in intermittent or continuous changes in lead impedance.

Short circuits, open circuits or significant changes in impedance may be referred to, in general, as lead-related conditions. In the case of cardiac leads, sensing of an intrinsic heart rhythm through a lead can be altered by lead-related conditions. Structural modifications to leads, conductors or electrodes may alter sensing integrity. Furthermore, impedance changes in the stimulation path due to lead-related conditions may affect sensing and stimulation integrity for pacing, cardioversion, or defibrillation. In addition to lead-related conditions, conditions associated with sensor devices or sensing circuitry may affect sensing integrity.

SUMMARY

In general, the disclosure relates to techniques for providing a combination of stored diagnostic information, including impedance trend data, into one displayable report that may be used to diagnose a potential condition with an implantable electrode lead. In addition to impedance trend data, the stored diagnostic information may include information about non-sustained episodes (such as a non-sustained tachycardia), electrogram (EGM) data associated with these non-sustained episodes, information about sensing integrity counts (SICs), and EGM data associated with these SICs. This information may then be provided in a single report, or user interface screen, that provides clinically actionable information based on a potential condition with an electrode lead. Annotations may also be provided on the report to highlight various report elements or possible conditions, such as, for example, abnormal EGM signals, impedances and/or heart rates. In some cases, the report may be automatically generated and provided to an end user.

In one embodiment, a method comprises obtaining impedance trend data for an electrical path, the electrical path comprising a plurality of electrodes, obtaining additional diagnostic data that is associated with the electrical path, the additional diagnostic data being distinct from the impedance trend data. The method further comprises combining both the impedance trend data and the additional diagnostic data into a displayable report that indicates whether there is a possible condition with the electrical path.

In one embodiment, an implantable medical device comprises one or more implantable medical electrode leads including a plurality of electrodes, and one or more processors. The one or more processors are configured to obtain impedance trend data for an electrical path, the electrical path comprising at least two of the plurality of electrodes, obtain additional diagnostic data that is associated with the electrical path, the additional diagnostic data being distinct from the impedance trend data, and combine both the impedance trend data and the additional diagnostic data into a report that indicates whether there is a possible condition with the electrical path.

In one embodiment, a device comprises an output device and one or more processors. The one or more processors are configured to obtain impedance trend data for an electrical path, the electrical path comprising a plurality of electrodes, obtain additional diagnostic data that is associated with the electrical path, the additional diagnostic data being distinct from the impedance trend data, and combine both the impedance trend data and the additional diagnostic data into a displayable report that indicates whether there is a possible condition with the electrical path.

In one embodiment, a computer-readable medium comprises instructions for causing one or more processors to obtain impedance trend data for an electrical path, the electrical path comprising a plurality of electrodes, obtain additional diagnostic data that is associated with the electrical path, the additional diagnostic data being distinct from the impedance trend data, and combine both the impedance trend data and the additional diagnostic data into a displayable report that indicates whether there is a possible condition with the electrical path.

The details of one or more embodiments of the disclosure are set forth in the accompanying drawings and the description below. Other features, objects, and advantages of the disclosure will be apparent from the description and drawings, and from the claims.

BRIEF DESCRIPTION OF DRAWINGS

FIG. 11 is a visual diagram illustrating an example of non-sustained episode data that may be displayed within the lead integrity report of FIG. 8.

DETAILED DESCRIPTION

Figure 1:
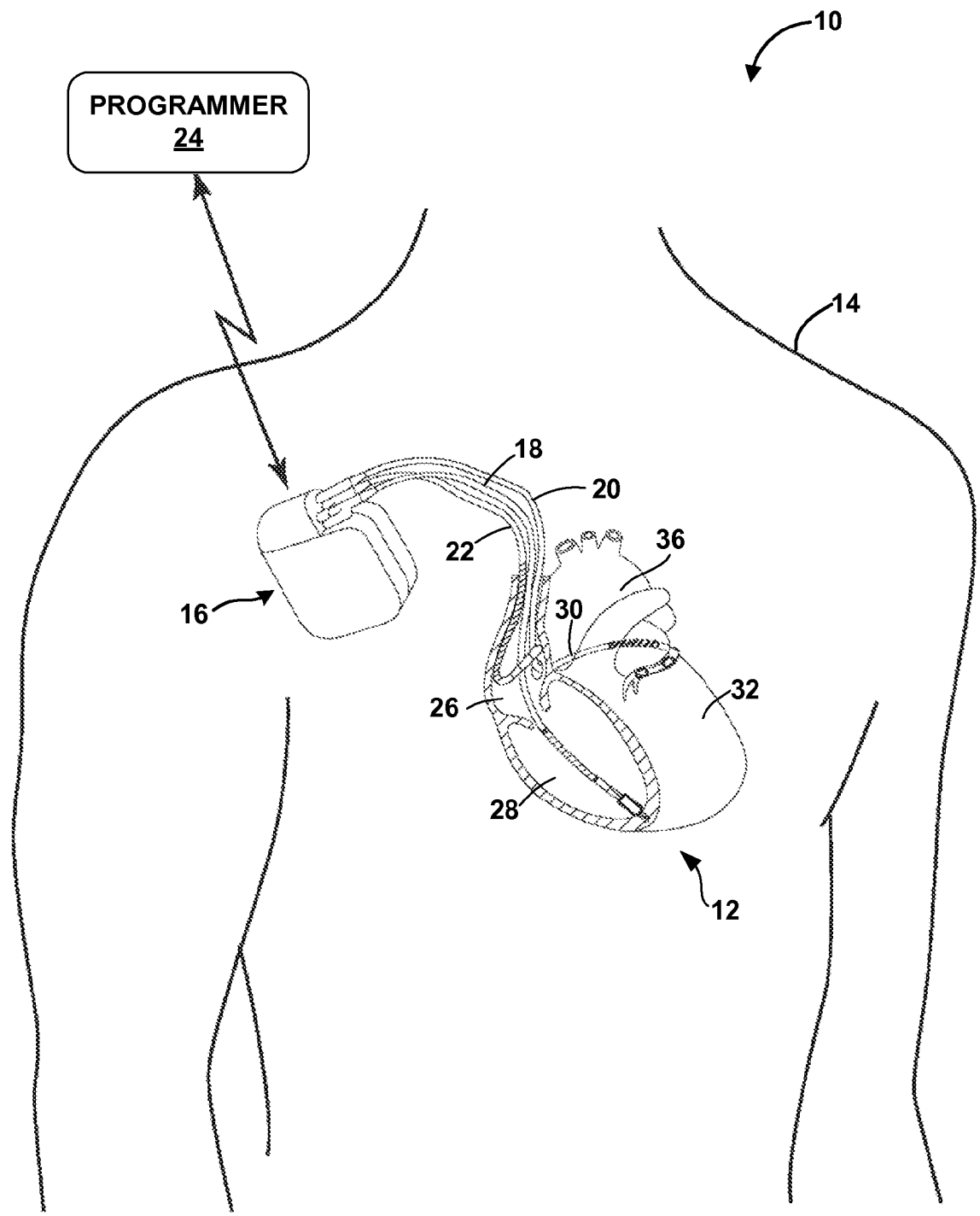
FIG. 1 is a conceptual diagram illustrating an example therapy system that may be used to provide therapy to a heart of a patient, according to one embodiment of the disclosure.

FIG. 1 is a conceptual diagram illustrating an example therapy system 10 that may be used to provide therapy to heart 12 of patient 14. Patient 12 ordinarily, but not necessarily, will be a human. Therapy system 10 includes IMD 16, which is coupled to leads 18, 20, and 22, and programmer 24. IMD 16 may be, for example, an implantable pacemaker, cardioverter, and/or defibrillator that provide electrical signals to heart 12 via electrodes coupled to one or more of leads 18, 20, and 22.

In one embodiment, IMD 16 may periodically collect and measure diagnostic data, including impedance data, associated with one or more of leads 18, 20, and 22. IMD 16 may provide this diagnostic data to programmer 24 via wireless telemetry. In addition to impedance data, the diagnostic data may include non-sustained episode data and sensing integrity data, which will be described in more detail below. IMD 16 and/or programmer 24 may combine all of the received diagnostic data in a single report that may identify a possible condition of one or more of leads 18, 20, and 22. The single report, which may be displayed on programmer 24, provides a combined set of clinically actionable diagnostic information to a clinician that may use programmer 24.

Various embodiments are described herein. Although many of the techniques that are described relate to cardiac therapy, these and other techniques could be applied to other therapies in which lead integrity may be important or relevant, such as, for example, spinal cord stimulation, deep brain stimulation, pelvic floor stimulation, gastric stimulation, occipital stimulation, or functional electrical stimulation.

Leads 18, 20, 22 extend into the heart 12 of patient 16 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

IMD 16 may sense electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar. IMD 16 may also provide defibrillation therapy and/or cardioversion therapy via electrodes located on at least one of the leads 18, 20, 22. IMD 16 may detect arrhythmia of heart 12, such as fibrillation of ventricles 28 and 32, and deliver defibrillation therapy to heart 12 in the form of electrical pulses. In some examples, IMD 16 may be programmed to deliver a progression of therapies, e.g., pulses with increasing energy levels, until a fibrillation of heart 12 is stopped. IMD 16 detects fibrillation employing one or more fibrillation detection techniques known in the art.

In some examples, programmer 24 may be a handheld computing device or a computer workstation. Programmer 24 may include a user interface that receives input from a user.

The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some embodiments, a display of programmer 24 may include a touch screen display, and a user may interact with programmer 24 via the display.

A user, such as a physician, technician, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD.

For example, the user may use programmer 24 to retrieve information from IMD 16 regarding the rhythm of heart 12, trends therein over time, or arrhythmic episodes. As another example, the user may use programmer 24 to retrieve information from IMD 16 regarding other sensed physiological parameters of patient 14, such as intracardiac or intravascular pressure, activity, posture, respiration, or thoracic impedance. As another example, the user may use programmer 24 to retrieve information from IMD 16 regarding the performance or integrity of IMD 16 or other components of system 10, such as leads 18, 20 and 22, or a power source of IMD 16.

The user may use programmer 24 to program a therapy progression, select electrodes used to deliver defibrillation pulses, select waveforms for the defibrillation pulse, or select or configure a fibrillation detection algorithm for IMD 16. The user may also use programmer 24 to program aspects of other therapies provided by IMD 14, such as cardioversion or pacing therapies. In some examples, the user may activate certain features of IMD 16 by entering a single command via programmer 24, such as depression of a single key or combination of keys of a keypad or a single point-and-select action with a pointing device.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

Figure 2:
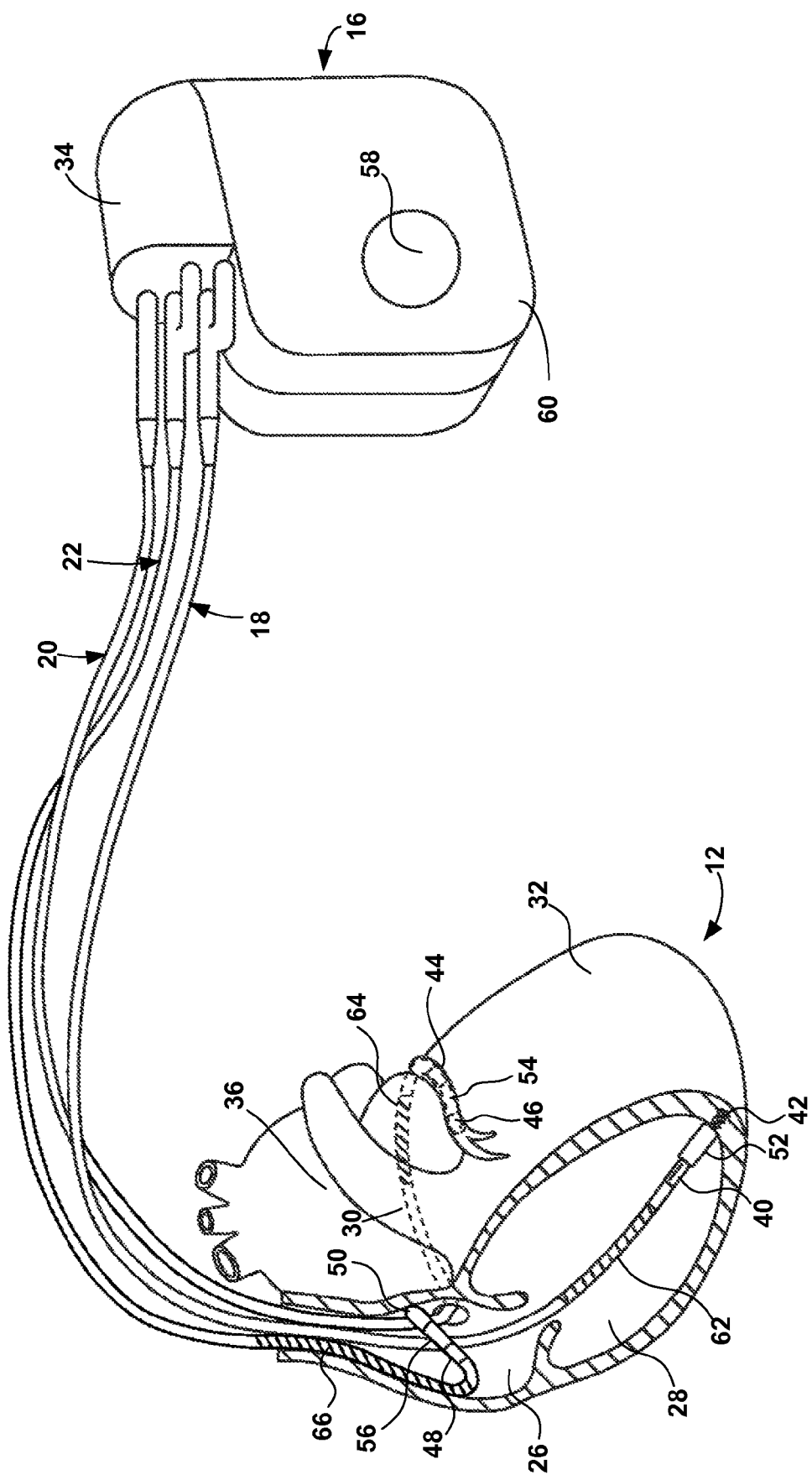
FIG. 2 is a conceptual diagram illustrating the implantable medical device (IMD) and the leads of the therapy system shown in FIG. 1 in greater detail, according to one embodiment.

In one embodiment, IMD 16 is capable of collecting diagnostic measurement data for one or more of electrode leads 18, 20, and 22. Upon collection of such measurement data, IMD 16 may provide such information to programmer 24. The diagnostic data may include impedance data, non-sustained episode data, and/or sensing integrity data. IMD 16 and/or programmer 24 may combine the collected diagnostic data into a single displayable report, which may be displayed to a clinician on programmer 24. The clinician may use or view the report when diagnosing a lead-related condition with an implantable electrode lead. Annotations may also be provided on the report to highlight various report elements or possible conditions, such as, for example, abnormal EGM signals, impedances and/or heart rates. The clinician may provide input to specify such annotations. In some cases, IMD 16 and/or programmer 24 may automatically provide certain annotations within the diagnostic data. FIG. 2 is a conceptual diagram illustrating IMD 16 and leads 18, 20, and 22 of therapy system 10 in greater detail. Leads 18, 20, 22 may be electrically coupled to a stimulation generator and a sensing module of IMD 16 via connector block 34. In some examples, proximal ends of leads 18, 20, 22 may include electrical contacts that electrically couple to respective electrical contacts within connector block 34. In addition, in some examples, leads 18, 20, 22 may be mechanically coupled to connector block 34 with the aid of set screws, connection pins or another suitable mechanical coupling mechanism.

Each of the leads 18, 20, 22 includes an elongated insulative lead body carrying a number of concentric coiled conductors separated from one another by tubular insulative sheaths. In some cases, each of the leads 18, 20, 22 may include cable conductors. Bipolar electrodes 40 and 42 are located adjacent to a distal end of lead 18. In addition, bipolar electrodes 44 and 46 are located adjacent to a distal end of lead 20 and bipolar electrodes 48 and 50 are located adjacent to a distal end of lead 22. Electrodes 40, 44 and 48 may take the form of ring electrodes, and electrodes 42, 46 and 50 may take the form of extendable helix tip electrodes mounted retractably within insulative electrode heads 52, 54 and 56, respectively. Each of the electrodes 40, 42, 44, 46, 48 and 50 may be electrically coupled to a respective one of the coiled conductors within the lead body of its associated lead 18, 20, 22, and thereby coupled to respective ones of the electrical contacts on the proximal end of leads 18, 20 and 22.

Electrodes 40, 42, 44, 46, 48 and 50 may sense electrical signals attendant to the depolarization and repolarization of heart 12. The electrical signals are conducted to IMD 16 via the respective leads 18, 20, 22. In some examples, IMD 16 also delivers pacing pulses via electrodes 40, 42, 44, 46, 48 and 50 to cause depolarization of cardiac tissue of heart 12. In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. Any of the electrodes 40, 42, 44, 46, 48 and 50 may be used for unipolar sensing or pacing in combination with housing electrode 58. As described in further detail with reference to FIG. 4, housing 60 may enclose a stimulation generator that generates cardiac pacing pulses and defibrillation shocks, as well as a sensing module for monitoring the patient's heart rhythm.

Leads 18, 20, 22 also include elongated electrodes 62, 64, 66, respectively, which may take the form of a coil. IMD 16 may deliver defibrillation pulses to heart 12 via any combination of elongated electrodes 62, 64, 66, and housing electrode 58. Electrodes 58, 62, 64, 66 may also be used to deliver cardioversion pulses to heart 12. Elongated electrodes 62, 64 and 66 may also be used to sense electrical activity of heart 12. For example, a bipolar electrode combination may include elongate electrode 62 and electrode 42. Electrodes 62, 64, 66 may be fabricated from any suitable electrically conductive material, such as, but not limited to, platinum, platinum alloy or other materials known to be usable in implantable defibrillation electrodes.

The configuration of therapy system 10 illustrated in FIGS. 1 and 2 is merely one example. In other examples, a therapy system may include epicardial leads and/or patch electrodes instead of or in addition to the transvenous leads 18, 20, 22 illustrated in FIG. 1. Further, IMD 16 need not be implanted within patient 14. In examples in which IMD 16 is not implanted in patient 14, IMD 16 may deliver defibrillation pulses and other therapies to heart 12 via percutaneous leads that extend through the skin of patient 14 to a variety of positions within or outside of heart 12.

In addition, in other examples, a therapy system may include any suitable number of leads coupled to IMD 16, and each of the leads may extend to any location within or proximate to heart 12. For example, other examples of therapy systems may include three transvenous leads located as illustrated in FIGS. 1 and 2, and an additional lead located within or proximate to left atrium 36. As another example, other examples of therapy systems may include a single lead that extends from IMD 16 into right atrium 26 or right ventricle 28, or two leads that extend into a respective one of the right ventricle 28 and right atrium 26. An example of this type of therapy system is shown in FIG. 3.

Figure 3:
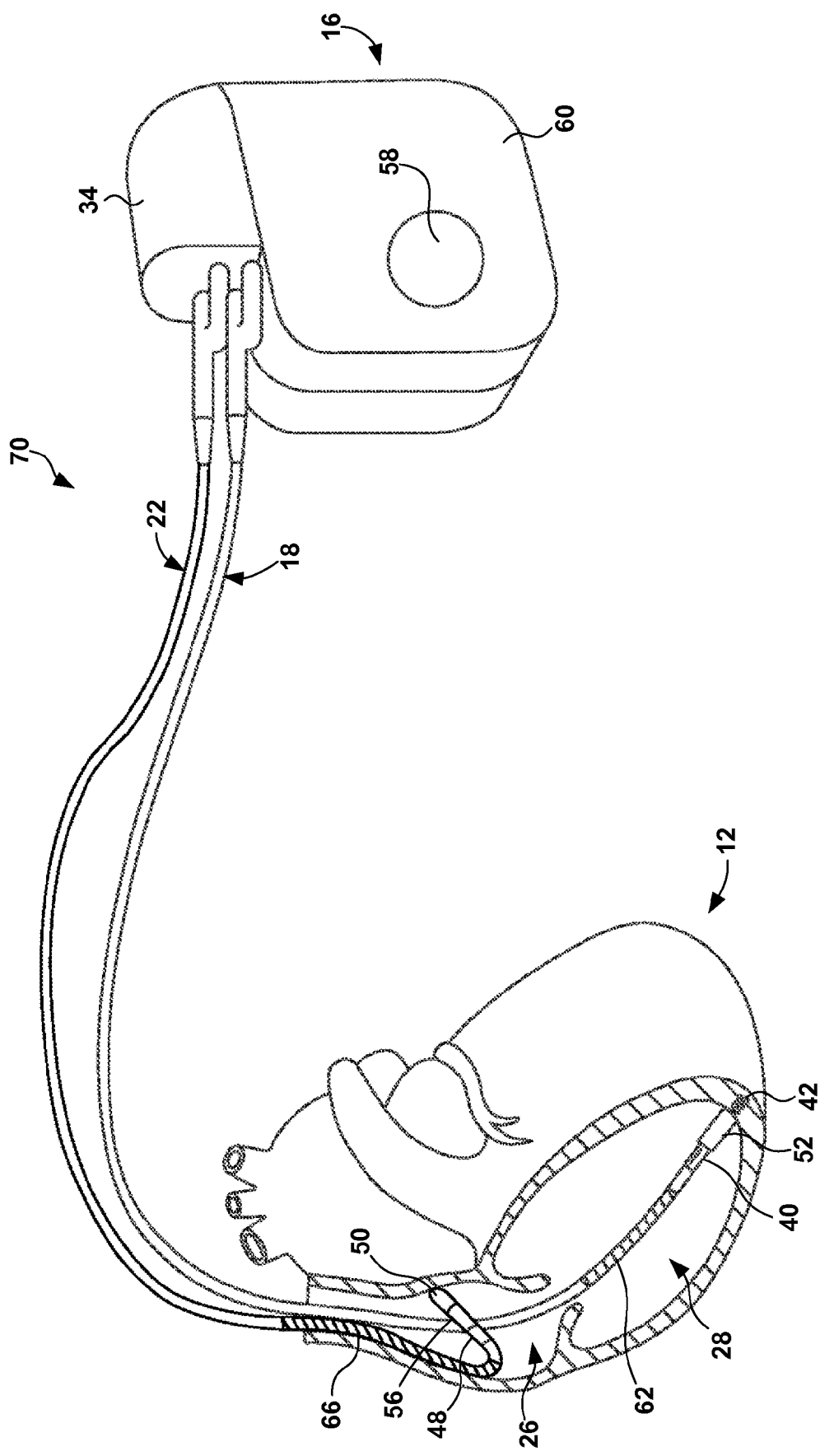
FIG. 3 is a conceptual diagram illustrating another example of a therapy system, which is similar to therapy system shown in FIGS. 1-2, but which includes two leads rather than three leads.

FIG. 3 is a conceptual diagram illustrating another example of therapy system 70, which is similar to therapy system 10 of FIGS. 1-2, but includes two leads 18, 22, rather than three leads. Leads 18, 22 are implanted within right ventricle 28 and right atrium 26, respectively. Therapy system 70 shown in FIG. 3 may be useful for providing defibrillation and pacing pulses to heart 12.

Figure 4:
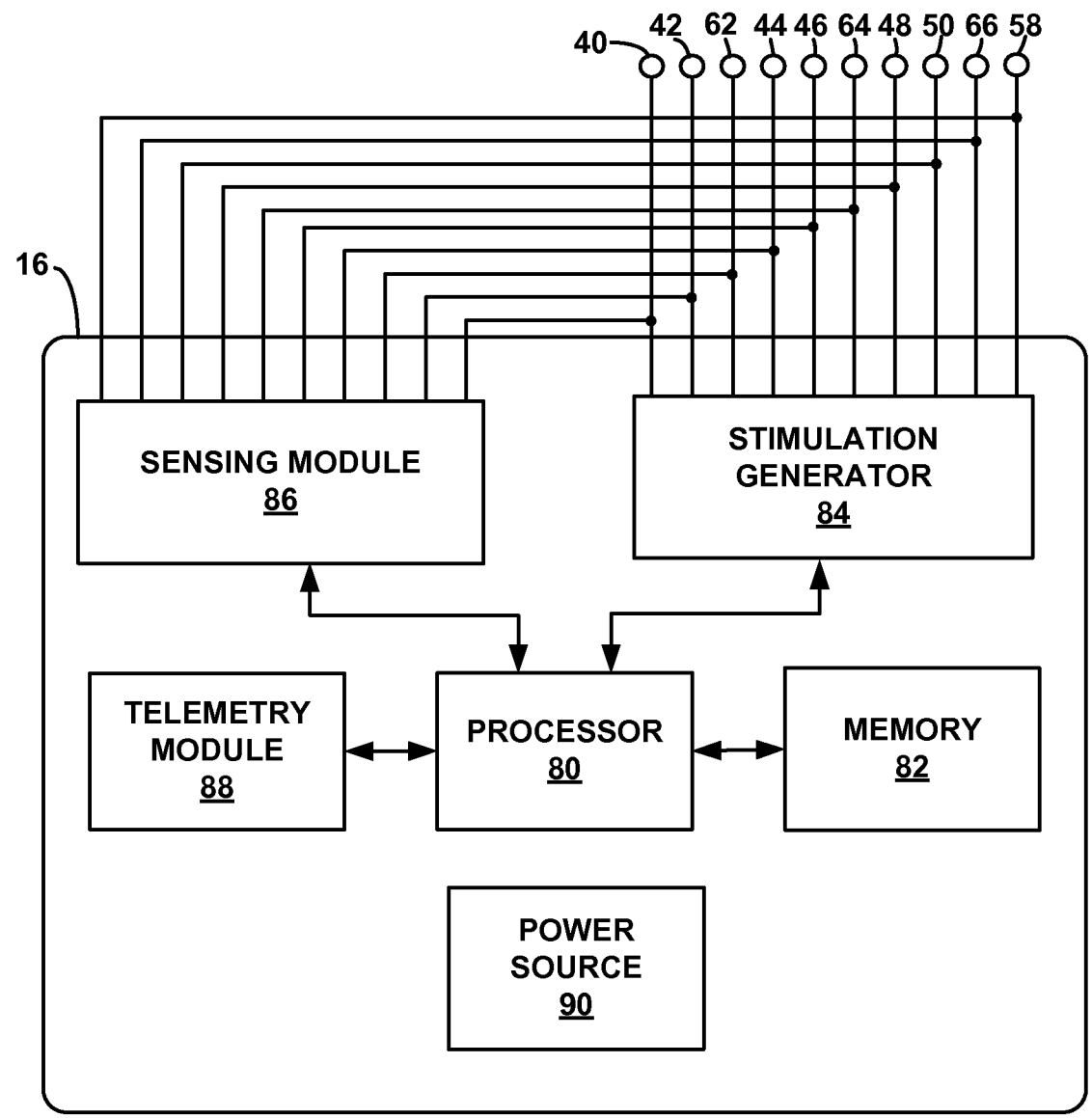
FIG. 4 is a functional block diagram of one example of the IMD shown in FIG. 1.

FIG. 4 is a functional block diagram of one example of IMD 16, which includes processor 80, memory 82, stimulation generator 84, sensing module 86, telemetry module 88, and power source 90. Processor 80 may comprise one or more processors. Memory 82 includes computer-readable instructions that, when executed by processor 80, cause IMD 16 and processor 80 to perform various functions attributed to IMD 16 and processor 80 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof. Processor 80 controls stimulation generator 84 to deliver stimulation therapy to heart 12 according to a selected one or more of therapy programs, which may be stored in memory 82. Specifically, processor 44 may control stimulation generator 84 to deliver electrical pulses with the amplitudes, pulse widths, frequency, or electrode polarities specified by the selected one or more therapy programs.

Stimulation generator 84 is electrically coupled to electrodes 40, 42, 44, 46, 48, 50, 58, 62, 64, and 66, e.g., via conductors of the respective lead 18, 20, 22, or, in the case of housing electrode 58, via an electrical conductor disposed within housing 60 of IMD 16. A switch matrix may also be provided to connect stimulation generator 84 to one or more of electrodes 40, 42, 44, 46, 48, 50, 58, 62, 64, and 66. Stimulation generator 84 is configured to generate and deliver electrical stimulation therapy to heart 12. For example, stimulation generator 84 may deliver defibrillation shocks to heart 12 via at least two electrodes 58, 62, 64, 66. Stimulation generator 84 may deliver pacing pulses via ring electrodes 40, 44, 48 coupled to leads 18, 20, and 22, respectively, and/or helical electrodes 42, 46, and 50 of leads 18, 20, and 22, respectively. In some examples, stimulation generator 84 delivers pacing, cardioversion, or defibrillation stimulation in the form of electrical pulses. In other examples, stimulation generator may deliver one or more of these types of stimulation in the form of other signals, such as sine waves, square waves, or other substantially continuous time signals.

Stimulation generator 84 may include a switch module and processor 80 may use the switch module to select, e.g., via a data/address bus, which of the available electrodes are used to deliver defibrillation pulses or pacing pulses. The switch module may include a switch array, switch matrix, multiplexer, or any other type of switching device suitable to selectively couple stimulation energy to selected electrodes.

Sensing module 86 monitors signals from at least one of electrodes 40, 42, 44, 46, 48, 50, 58, 62, 64 or 66 in order to monitor electrical activity of heart 12, e.g., via electrocardiogram (ECG) signals. Sensing module 86 may also include a switch module to select which of the available electrodes are used to sense the heart activity. In some examples, processor 80 may select the electrodes that function as sense electrodes via the switch module within sensing module 86, e.g., by providing signals via a data/address bus. In some examples, sensing module 86 includes one or more sensing channels, each of which may comprises an amplifier. In response to the signals from processor 80, the switch module of within sensing module 86 may couple the outputs from the selected electrodes to one of the sensing channels.

In some examples, one channel of sensing module 86 may include an R-wave amplifier that receives signals from electrodes 40 and 42, which are used for pacing and sensing in right ventricle 28 of heart 12. Another channel may include another R-wave amplifier that receives signals from electrodes 44 and 46, which are used for pacing and sensing proximate to left ventricle 32 of heart 12. In some examples, the R-wave amplifiers may take the form of an automatic gain controlled amplifier that provides an adjustable sensing threshold as a function of the measured R-wave amplitude of the heart rhythm.

In addition, in some examples, one channel of sensing module 86 may include a P-wave amplifier that receives signals from electrodes 48 and 50, which are used for pacing and sensing in right atrium 26 of heart 12. In some examples, the P-wave amplifier may take the form of an automatic gain controlled amplifier that provides an adjustable sensing threshold as a function of the measured P-wave amplitude of the heart rhythm. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Other amplifiers may also be used. Furthermore, in some examples, one or more of the sensing channels of sensing module 84 may be selectively coupled to housing electrode 58, or elongated electrodes 62, 64, or 66, with or instead of one or more of electrodes 40, 42, 44, 46, 48 or 50, e.g., for unipolar sensing of R-waves or P-waves in any of chambers 26, 28, 36, or 32 of heart 12.

In some examples, sensing module 84 includes a channel that comprises an amplifier with a relatively wider pass band than the R-wave or P-wave amplifiers. Signals from the selected sensing electrodes that are selected for coupling to this wide-band amplifier may be provided to a multiplexer, and thereafter converted to multi-bit digital signals by an analog-to-digital converter for storage in memory 82 as an electrogram (EGM). In some examples, the storage of such EGMs in memory 82 may be under the control of a direct memory access circuit. Processor 80 may employ digital signal analysis techniques to characterize the digitized signals stored in memory 82 to detect and classify the patient's heart rhythm from the electrical signals. Processor 80 may detect and classify the patient's heart rhythm by employing any of the numerous signal processing methodologies known in the art.

If IMD 16 is configured to generate and deliver pacing pulses to heart 12, processor 80 may include pacer timing and control module, which may be embodied as hardware, firmware, software, or any combination thereof. The pacer timing and control module may comprise a dedicated hardware circuit, such as an ASIC, separate from other processor 80 components, such as a microprocessor, or a software module executed by a component of processor 80, which may be a microprocessor or ASIC. The pacer timing and control module may include programmable counters which control the basic time intervals associated with DDD, VVI, DVI, VDD, AAI, DDI, DDDR, VVIR, DVIR, VDDR, AAIR, DDIR and other modes of single and dual chamber pacing. In the aforementioned pacing modes, "D" may indicate dual chamber, "V" may indicate a ventricle, "I" may indicate inhibited pacing (e.g., no pacing), and "A" may indicate an atrium. The first letter in the pacing mode may indicate the chamber that is paced, the second letter may indicate the chamber that is sensed, and the third letter may indicate the chamber in which the response to sensing is provided.

Intervals defined by the pacer timing and control module within processor 80 may include atrial and ventricular pacing escape intervals, refractory periods during which sensed P-waves and R-waves are ineffective to restart timing of the escape intervals, and the pulse widths of the pacing pulses. As another example, the pace timing and control module may define a blanking period, and provide signals sensing module 86 to blank one or more channels, e.g., amplifiers, for a period during and after delivery of electrical stimulation to heart 12. The durations of these intervals may be determined by processor 80 in response to stored data in memory 82. The pacer timing and control module of processor 80 may also determine the amplitude of the cardiac pacing pulses.

During pacing, escape interval counters within the pacer timing/control module of processor 80 may be reset upon sensing of R-waves and P-waves. Stimulation generator 84 may include pacer output circuits that are coupled, e.g., selectively by a switching module, to any combination of electrodes 40, 42, 44, 46, 48, 50, 58, 62, or 66 appropriate for delivery of a bipolar or unipolar pacing pulse to one of the chambers of heart 12. Processor 80 may reset the escape interval counters upon the generation of pacing pulses by stimulation generator 84, and thereby control the basic timing of cardiac pacing functions, including anti-tachyarrhythmia pacing.

The value of the count present in the escape interval counters when reset by sensed R-waves and P-waves may be used by processor 80 to measure the durations of R-R intervals, P-P intervals, PR intervals and R-P intervals, which are measurements that may be stored in memory 82. Processor 80 may use the count in the interval counters to detect an arrhythmia event, such as ventricular fibrillation or ventricular tachycardia.

In some examples, processor 80 may operate as an interrupt driven device, and is responsive to interrupts from pacer timing and control module, where the interrupts may correspond to the occurrences of sensed P-waves and R-waves and the generation of cardiac pacing pulses. Any necessary mathematical calculations to be performed by processor 80 and any updating of the values or intervals controlled by the pacer timing and control module of processor 80 may take place following such interrupts. A portion of memory 82 may be configured as a plurality of recirculating buffers, capable of holding series of measured intervals, which may be analyzed by processor 80 in response to the occurrence of a pace or sense interrupt to determine whether the patient's heart 12 is presently exhibiting atrial or ventricular tachyarrhythmia.

In some examples, an arrhythmia detection method may include any suitable tachyarrhythmia detection algorithms. In one example, processor 80 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND GREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND GREATMENT OF ARRHYTHMIAS," which issued on May 26, 1998. U.S. Pat. No. 5,545,186 to Olson et al. U.S. Pat. No. 5,755,736 to Gillberg et al. are incorporated herein by reference in their entireties. However, other arrhythmia detection methodologies may also be employed by processor 80 in other examples.

In the event that processor 80 detects an atrial or ventricular tachyarrhythmia based on signals from sensing module 86, and an anti-tachyarrhythmia pacing regimen is desired, timing intervals for controlling the generation of anti-tachyarrhythmia pacing therapies by stimulation generator 84 may be loaded by processor 80 into the pacer timing and control module to control the operation of the escape interval counters therein and to define refractory periods during which detection of R-waves and P-waves is ineffective to restart the escape interval counters.

If IMD 16 is configured to generate and deliver defibrillation pulses to heart 12, stimulation generator 84 may include a high voltage charge circuit and a high voltage output circuit. If IMD 16 is configured to generate and deliver pacing pulses to heart 12, stimulation generator 84 may include a low voltage charge circuit and a low voltage output circuit. In the event that generation of a cardioversion or defibrillation pulse is required, processor 80 may employ the escape interval counter to control timing of such cardioversion and defibrillation pulses, as well as associated refractory periods. In response to the detection of atrial or ventricular fibrillation or tachyarrhythmia requiring a cardioversion pulse, processor 80 may activate a cardioversion/defibrillation control module, which may, like pacer timing and control module, be a hardware component of processor 80 and/or a firmware or software module executed by one or more hardware components of processor 80. The cardioversion/defibrillation control module may initiate charging of the high voltage capacitors of the high voltage charge circuit of stimulation generator 84 under control of a high voltage charging control line.

Processor 80 may monitor the voltage on the high voltage capacitor may be monitored, e.g., via a voltage charging and potential (VCAP) line. In response to the voltage on the high voltage capacitor reaching a predetermined value set by processor 80, processor 80 may generate a logic signal that terminates charging. Thereafter, timing of the delivery of the defibrillation or cardioversion pulse by stimulation generator 84 is controlled by the cardioversion/defibrillation control module of processor 80. Following delivery of the fibrillation or tachycardia therapy, processor 80 may return stimulation generator 84 to a cardiac pacing function and await the next successive interrupt due to pacing or the occurrence of a sensed atrial or ventricular depolarization.

Stimulation generator 84 may deliver cardioversion or defibrillation pulses with the aid of an output circuit that determines whether a monophasic or biphasic pulse is delivered, whether housing electrode 58 serves as cathode or anode, and which electrodes are involved in delivery of the cardioversion or defibrillation pulses. Such functionality may be provided by one or more switches or a switching module of stimulation generator 84.

Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and the control signals for the telemetry circuit within telemetry module 88, e.g., via an address/data bus. In some examples, telemetry module 88 may provide received data to processor 80 via a multiplexer.

In some examples, processor 80 may transmit atrial and ventricular heart signals (e.g., electrocardiogram signals) produced by atrial and ventricular sense amp circuits within sensing module 86 to programmer 24. Programmer 24 may interrogate IMD 16 to receive the heart signals. Processor 80 may store heart signals within memory 82, and retrieve stored heart signals from memory 82. Processor 80 may also generate and store marker codes indicative of different cardiac events that sensing module 86 detects, and transmit the marker codes to programmer 24. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety.

The various components of IMD 16 are coupled to power source 90, which may include a rechargeable or non-rechargeable battery. A non-rechargeable battery may be selected to last for several years, while a rechargeable battery may be inductively charged from an external device, e.g., on a daily or weekly basis.

In one embodiment, sensing module 86 is capable of collecting, or measuring, diagnostic data (such as impedance data, non-sustained episode data, and/or sensing integrity data) for each of leads 18, 20, and 22. In this embodiment, sensing module 86 and/or processor 80 measure impedance values during delivery of an electrical signal between at least two electrodes that are coupled to one or more of leads 18, 20 and 22. Processor 80 may control signal generator 84 to deliver the electrical signal between the electrodes. For example, sensing module 86 and/or processor 80 may collect, measure, and/or calculate impedance data for lead 18 based on delivery of an electrical signal between electrodes 40 and 42, impedance data for lead 20 based on delivery of an electrical signal between electrodes 44 and 46, and impedance data for lead 22 based on delivery of an electrical signal between electrodes 48 and 50. Sensing module 86 and/or processor 80 may collect, measure, and/or calculate impedance values for any of a variety of electrical paths that include one or more electrodes on one or more of leads 18, 20, and 22 based on delivery of a signal between any combination of two or more of electrodes 40, 42, 44, 46 and 48, elongated electrodes 62, 64 and 66, and housing electrode 58. IMD 16 may store measured impedance values in memory 82. Sensing module 86 may be used to assist in the measurement of other diagnostic information for leads 18, 20, and 22, as well, such as non-sustained episode data and/or sensing integrity data. IMD 16 may send diagnostic data to programmer 24 via telemetry module 88.

In some examples, IMD 16 may perform an impedance measurement by delivering, from stimulation generator 84, a voltage pulse between first and second electrodes, and measuring a resulting current. IMD 16, e.g., processor 80, may calculate a resistance based upon the voltage amplitude of the pulse and the measured amplitude of the resulting current. In these examples, stimulation generator 84 delivers signals that do not necessarily deliver stimulation therapy to heart 12, due to, for example, the amplitudes of such signals and/or the timing of delivery of such signals. For example, these signals may comprise sub-threshold amplitude signals that may not stimulate heart 12. In some cases, these signals may be delivered during a refractory period, in which case they also may not stimulate heart 12.

In some examples, IMD 16 may be entirely dedicated to monitoring and/or impedance measurements, i.e., the techniques described herein are not limited to implantation in devices that deliver stimulation or any other type of therapy. In these examples, stimulation generator 84 may be configured to deliver signals that do not deliver stimulation therapy to heart 12.

In certain cases, IMD 16 may perform impedance measurement by delivering, from stimulation generator 84, a current pulse across first and second electrodes, and measuring a resulting voltage. IMD 16 may calculate a resistance based upon the current amplitude of the pulse and the measured amplitude of the resulting voltage. Sensing module 86 may include circuitry for measuring amplitudes of resulting currents or voltages, such as sample and hold circuitry. IMD 16 may use defined or predetermined pulse amplitudes, widths, frequencies, or electrode polarities for the pulses delivered for these various impedance measurements. In some examples, the amplitudes and/or widths of the pulses may be sub-threshold, e.g., below a threshold necessary to capture or otherwise activate tissue, such as cardiac tissue.

In certain cases, IMD 16 may collect impedance values that include both a resistive and a reactive (i.e., phase) component. In such cases, IMD 16 may measure impedance during delivery of a sinusoidal or other time varying signal by signal generator 84, for example. Thus, as used herein, the term "impedance" is used in a broad sense to indicate any collected, measured, and/or calculated value that may include one or both of resistive and reactive components. Impedance data may include actual, measured impedance values, or may include values that can be used to calculate impedance (such as current and/or voltage values).

In one embodiment, IMD 16 may analyze the measured impedance values, and may compare these values, or other computed values, to determined thresholds and identify any possible conditions with one or more of leads 18, 20 and 22. For example, IMD 16 may, as a result of one or more comparisons, determine that one or more of leads 18, 20, and 22 has a lead-related condition. IMD 16 may send impedance measurement and/or analysis data to programmer 24 via telemetry module 88.

Figure 5:
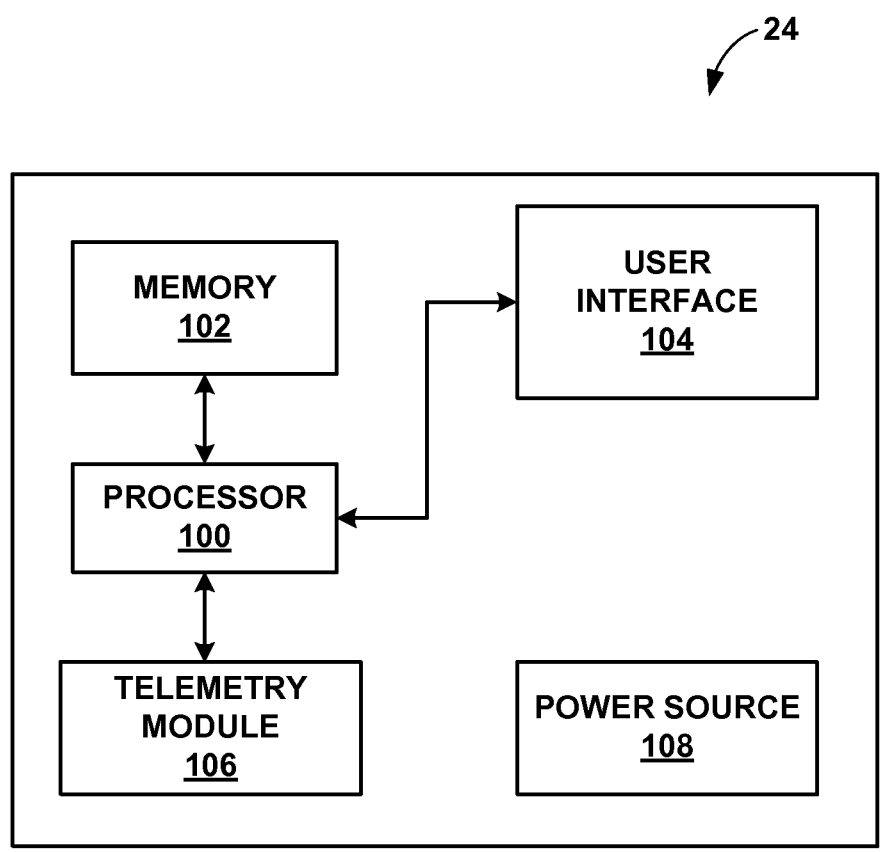
FIG. 5 is block diagram of an example of the programmer shown in FIG. 1, according to one embodiment.

FIG. 5 is block diagram of an example programmer 24. As shown in FIG. 5, programmer 24 includes processor 100, memory 102, user interface 104, telemetry module 106, and power source 108. Processor 100 may comprise one or more processors. Programmer 24 may be a dedicated hardware device with dedicated software for programming of IMD 16. Alternatively, programmer 24 may be an off-the-shelf computing device running an application that enables programmer 24 to program IMD 16.

A user may use programmer 24 to select therapy programs (e.g., sets of stimulation parameters), generate new therapy programs, modify therapy programs through individual or global adjustments or transmit the new programs to a medical device, such as IMD 16 (FIG. 1). The clinician may interact with programmer 24 via user interface 104, which may include display to present graphical user interface to a user, and a keypad or another mechanism for receiving input from a user.

Processor 100 can take the form one or more microprocessors, DSPs, ASICs, FPGAs, programmable logic circuitry, or the like, and the functions attributed to processor 102 herein may be embodied as hardware, firmware, software or any combination thereof. Memory 102 may store instructions that cause processor 100 to provide the functionality ascribed to programmer 24 herein, and information used by processor 100 to provide the functionality ascribed to programmer 24 herein. Memory 102 may include any fixed or removable magnetic, optical, or electrical media, such as RAM, ROM, CD-ROM, hard or floppy magnetic disks, EEPROM, or the like. Memory 102 may also include a removable memory portion that may be used to provide memory updates or increases in memory capacities. A removable memory may also allow patient data to be easily transferred to another computing device, or to be removed before programmer 24 is used to program therapy for another patient. Memory 102 may also store information that controls therapy delivery by IMD 16, such as stimulation parameter values.

Programmer 24 may communicate wirelessly with IMD 16, such as using RF communication or proximal inductive interaction. This wireless communication is possible through the use of telemetry module 102, which may be coupled to an internal antenna or an external antenna. An external antenna that is coupled to programmer 24 may correspond to the programming head that may be placed over heart 12, as described above with reference to FIG. 1. Telemetry module 102 may be similar to telemetry module 88 of IMD 16 (FIG. 4).

Telemetry module 102 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection.

Power source 108 delivers operating power to the components of programmer 24. Power source 108 may include a battery and a power generation circuit to produce the operating power. In some embodiments, the battery may be rechargeable to allow extended operation. Recharging may be accomplished by electrically coupling power source 108 to a cradle or plug that is connected to an alternating current (AC) outlet. In addition or alternatively, recharging may be accomplished through proximal inductive interaction between an external charger and an inductive charging coil within programmer 24. In other embodiments, traditional batteries (e.g., nickel cadmium or lithium ion batteries) may be used. In addition, programmer 24 may be directly coupled to an alternating current outlet to power programmer 24. Power source 104 may include circuitry to monitor power remaining within a battery. In this manner, user interface 104 may provide a current battery level indicator or low battery level indicator when the battery needs to be replaced or recharged. In some cases, power source 108 may be capable of estimating the remaining time of operation using the current battery.

In one embodiment, programmer 24 may receive diagnostic measurement data from IMD 16 via telemetry module 106. As described previously, IMD 16 may periodically collect impedance measurement data, as well as other diagnostic data, for one or more of leads 18, 20, and 22. In certain cases, programmer 24 may combine all of the received diagnostic information into a single lead integrity report, as will be described in more detail below. Programmer 24 may display the lead integrity report to a user, such as clinician, via user interface 104.

Figure 6:
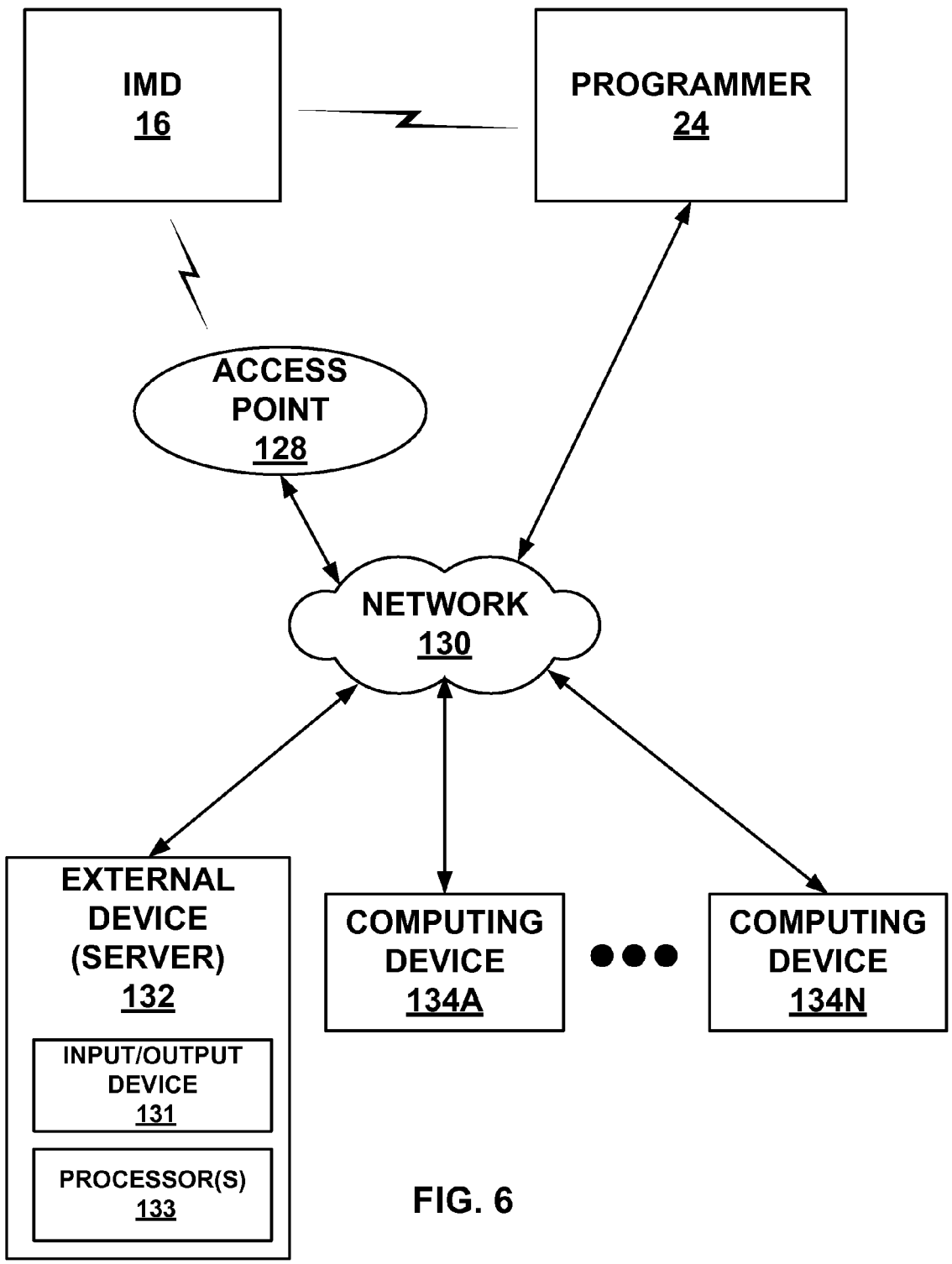
FIG. 6 is a block diagram illustrating an external device, such as a server, and one or more computing devices that are coupled to the IMD and programmer shown in FIG. 1 via a network, according to one embodiment.

FIG. 6 is a block diagram illustrating an external device 132, such as a server, and one or more computing devices 134A-134N that are coupled to IMD 16 and programmer 24 shown in FIG. 1 via a network 130, according to one embodiment. In this embodiment, IMD 16 uses its telemetry module 88 to communicate with programmer 24 via a first wireless connection, and to communication with an access point 128 via a second wireless connection. In some cases, IMD 16 may communicate with other access points, programmers, and/or computing devices (not shown) that are co-located with patient 14 via one or more wireless connections.

In the example of FIG. 6, access point 128, programmer 24, external device 132, and computing devices 134A-134N are interconnected, and able to communicate with each other, through network 130. In some cases, one or more of access point 128, programmer 24, external device 132, and computing devices 134A-134N may be coupled to network 130 through one or more wireless connections. IMD 16, programmer 24, external device 132, and computing devices 134A-134N may each comprise one or more processors, such as one or more microprocessors, DSPs, ASICs, FPGAs, programmable logic circuitry, or the like, that may perform various functions and operations, such as those described herein. In some embodiments, additional access points, programmers, and/or computing devices that are coupled to IMD 16 and co-located with patient 14 (not shown) may also each comprise one or more processors, such as one or more microprocessors, DSPs, ASICs, FPGAs, programmable logic circuitry, or the like, that may perform various functions and operations, such as those described herein.

Access point 128 may comprise a device that connects to network 130 via any of a variety of connections, such as telephone dial-up, digital subscriber line (DSL), or cable modem connections. In other embodiments, access point 128 may be coupled to network 130 through different forms of connections, including wired or wireless connections. In some embodiments, access point 128 may be co-located with patient 14 and may comprise one or more programming units and/or computing devices (e.g., one or more monitoring units) that may perform various functions and operations described herein. For example, access point 128 may include a home-monitoring unit that is co-located with patient 14 and that may monitor the activity of IMD 16.

During operation, IMD 16 may collect, measure, and store various forms of diagnostic data. For example, as described previously, IMD 16 may collect impedance measurement data for one or more electrical paths associated with one or more of leads 18, 20, and 22. Each electrical path may include a plurality of electrodes associated with the one or more leads. In certain cases, IMD 16 may directly analyze collected diagnostic data and generate any corresponding reports or alerts, and also possible annotations. In some cases, however, IMD 16 may send diagnostic data to programmer 24 and/or external device 132, either wirelessly or via access point 128 and network 130, for remote processing and analysis.

For example, IMD 16 may send programmer 24 collected impedance measurement data, non-sustained episode data, and/or sensing integrity data, which is then analyzed by programmer 24. Programmer 24 may generate reports or alerts after analyzing this diagnostic data and determining that there may be a possible condition with one or more of the electrical paths for leads 18, 20, and/or 22. Programmer 24 may also provide annotations to the report and/or alert, such as annotations that are described in more detail below. In some cases, programmer 24 may determine which portions of the impedance measurement data, non-sustained episode data, and/or sensing integrity data that is to be included within a report and/or alert.

In some cases, IMD 16 and/or programmer 24 may combine all of the diagnostic data into a single displayable lead integrity report, which may be displayed on programmer 24. The lead integrity report contains diagnostic information concerning one or more electrode leads that are coupled to IMD 16, such as leads 18, 20, or 22, and may also include annotations that have automatically been provided by IMD 16 and/or programmer 24. A clinician or other trained professional may review and/or further annotate the lead integrity report, and possibly identify any lead-related conditions.

In another example, IMD 16 may provide external device 132 with collected diagnostic data via access point 128 and network 130. External device 132 includes one or more processors 133. In some cases, external device 132 may request such data, and in some cases, IMD 16 may automatically or periodically provide such data to external device 132. Upon receipt of the diagnostic data via input/output device 131, external device 132 is capable of analyzing the data and generating reports or alerts upon determination that there may be a possible condition with one or more electrical paths for leads 18, 20, and/or 22. In one embodiment, external device 132 may combine selected diagnostic data into a lead integrity report, which may include one or more annotations provided by external device 132. One or more of computing devices 134A-134N may access the report through network 130 and display the report to users of computing devices 134A-134N. In some cases, external device 132 may automatically send the report via input/output device 131 to one or more of computing devices 134A-134N as an alert, such as an audio or visual alert. In some cases, external device 132 may send the report to another device, such as programmer 24, either automatically or upon request. In some cases, external device 132 may display the report to a user via input/output device 131.

In one embodiment, external device 132 may comprise a secure storage site for diagnostic information that has been collected from IMD 16 and/or programmer 24. In this embodiment, network 130 may comprise an Internet network, and trained professionals, such as clinicians, may use computing devices 134A-134N to securely access stored diagnostic data on external device 132. For example, the trained professionals may need to enter usernames and passwords to access the stored information on external device 132. In one embodiment, external device 132 may be a CareLink® server provided by Medtronic, Inc., of Minneapolis, Minn.

Figure 7:
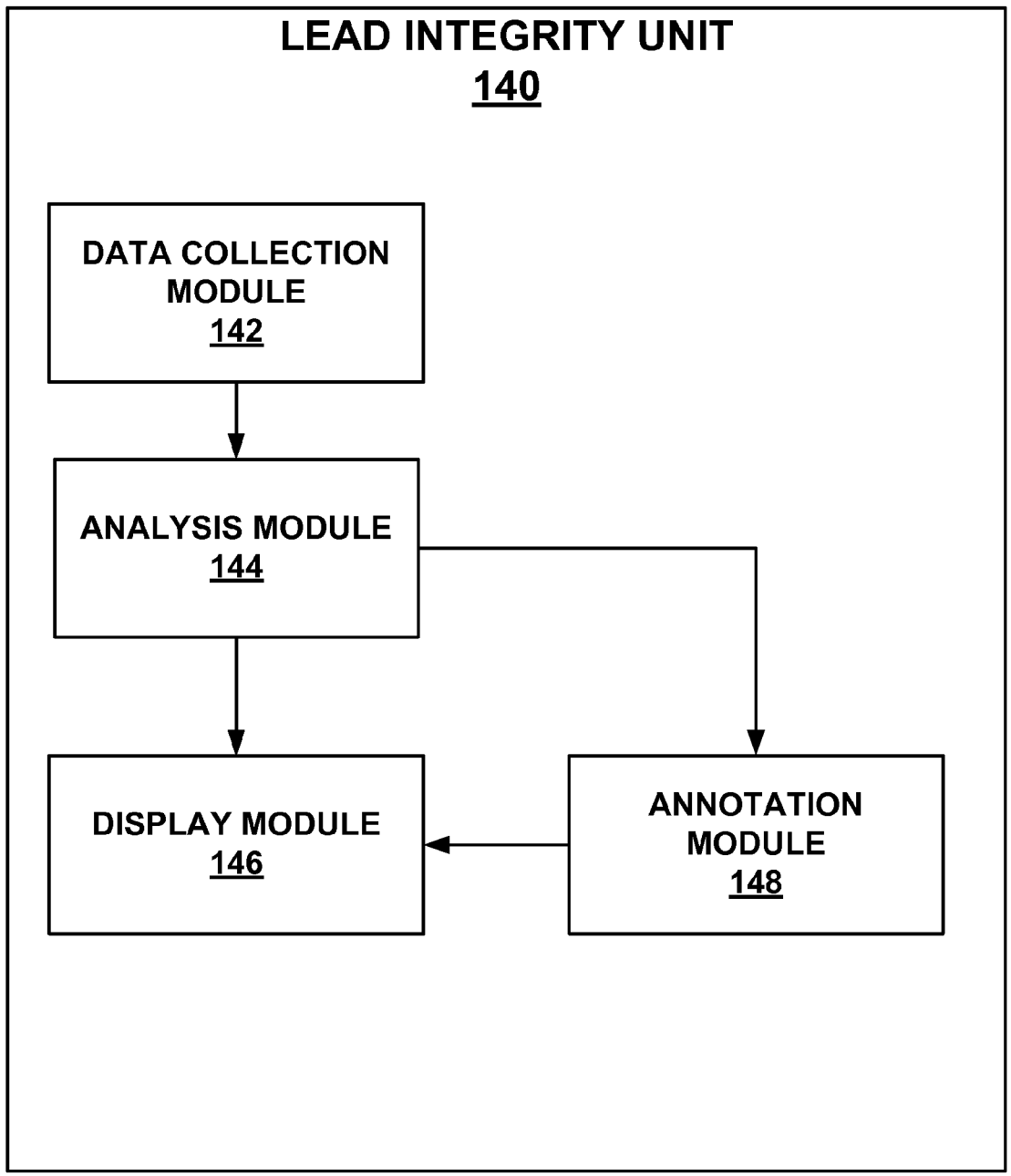
FIG. 7 is a block diagram illustrating multiple modules of a lead integrity functional unit, according to one embodiment.

FIG. 7 is a block diagram illustrating multiple modules of a lead integrity functional unit 140, according to one embodiment. In this embodiment, each module 142, 144, 146, and 148 of lead integrity unit 140 may be implemented in one or more processors, such as processor 80 of IMD 16, processor 100 of programmer 24, and/or processor(s) 133 of external device 132 to provide the functionality of lead integrity unit 140. Lead integrity unit 140 may provide a lead integrity report, such as lead integrity report 150, which may be reviewed or used by a clinician to identify possible lead-related conditions.

As shown in FIG. 7, lead integrity unit 140 includes a data collection module 142, an analysis module 144, a display module 146, and an annotation module 148. Data collection module 142 may collect various forms of diagnostic data associated with one or more electrical paths associated with one or more leads. Each electrical path may comprise a plurality of electrodes associated with the one or more leads. For example, data collection module 142 may measure the diagnostic data, or may obtain the data from a device, such as IMD 16. The diagnostic data may include impedance trend data, non-sustained episode data, and/or sensing integrity data. In some cases, the diagnostic data may also include electrogram (EGM) data, which may be associated with the non-sustained episode data, sensing integrity data, and/or impedance trend data. Within the EGM data, abnormal trends with P-waves and/or R-waves (e.g., abnormal duration and/or amplitude) may be an indication of a lead condition. In addition, abnormal pacing threshold trends may also be an indication of a lead condition. (A pacing threshold is typically a minimum amount of energy needed to make the heart beat consistently.)

Analysis module 144 analyzes the data collected by data collection module 142. In some cases, analysis module 144 may analyze the lead-related diagnostic data in an attempt to identify any possible lead conditions. Analysis module 144 may look for certain trends in the data, or data points that may serve as statistical outliers with respect to the other collected data. Analysis module 144 may also compare certain portions of the diagnostic data to defined or predetermined thresholds during its analysis, in an effort to uncover any trends or potential lead-related conditions. In certain cases, analysis module 144 may determine whether and/or when to generate a report or alarm that includes the diagnostic data and/or any annotations that may automatically be provided by analysis module 144 to the data.

Display module 146 is capable of displaying the diagnostic data, such as impedance trend data 152, non-sustained episode data 154, and/or sensing integrity data 156 within a lead integrity report 150. The collected diagnostic information related to one or more leads may be provided, or displayed, within this lead integrity report 150. In particular, display module 146 may use the output of analysis module 144 when preparing a display of lead integrity report 150. For example, display module 146 may display specific information determined to be relevant or important by analysis module 144, or information that would otherwise be helpful to a clinician viewing the lead integrity report 150 when attempting to identify potential electrical path and/or lead-related issues.

Display module 146 may also display certain annotations within lead integrity report 150 that are provided by annotation module 148. Annotation module 148 may provide various forms of visual and/or audio annotations to data contained within lead integrity report 150. For example, when lead integrity report 150 is displayed to a user, annotation module 148 may graphically annotate one or more portions of the impedance trend data 152, non-sustained episode data 154, and/or sensing integrity data 156 to highlight particular data elements or portions for review by the user. In certain cases, annotation module 148 may automatically provide annotations to lead integrity report 150 based upon information provided by analysis module 144. In these cases, annotation module 148 may annotate certain data within lead integrity report 150 that has been identified or possibly flagged as important or relevant by analysis module 144. In certain cases, annotation module 148 may provide annotations based upon input received by the user (such as a clinician) who manually provides such annotations. A lead integrity report may be provided for each of a plurality of leads.

Figure 8:
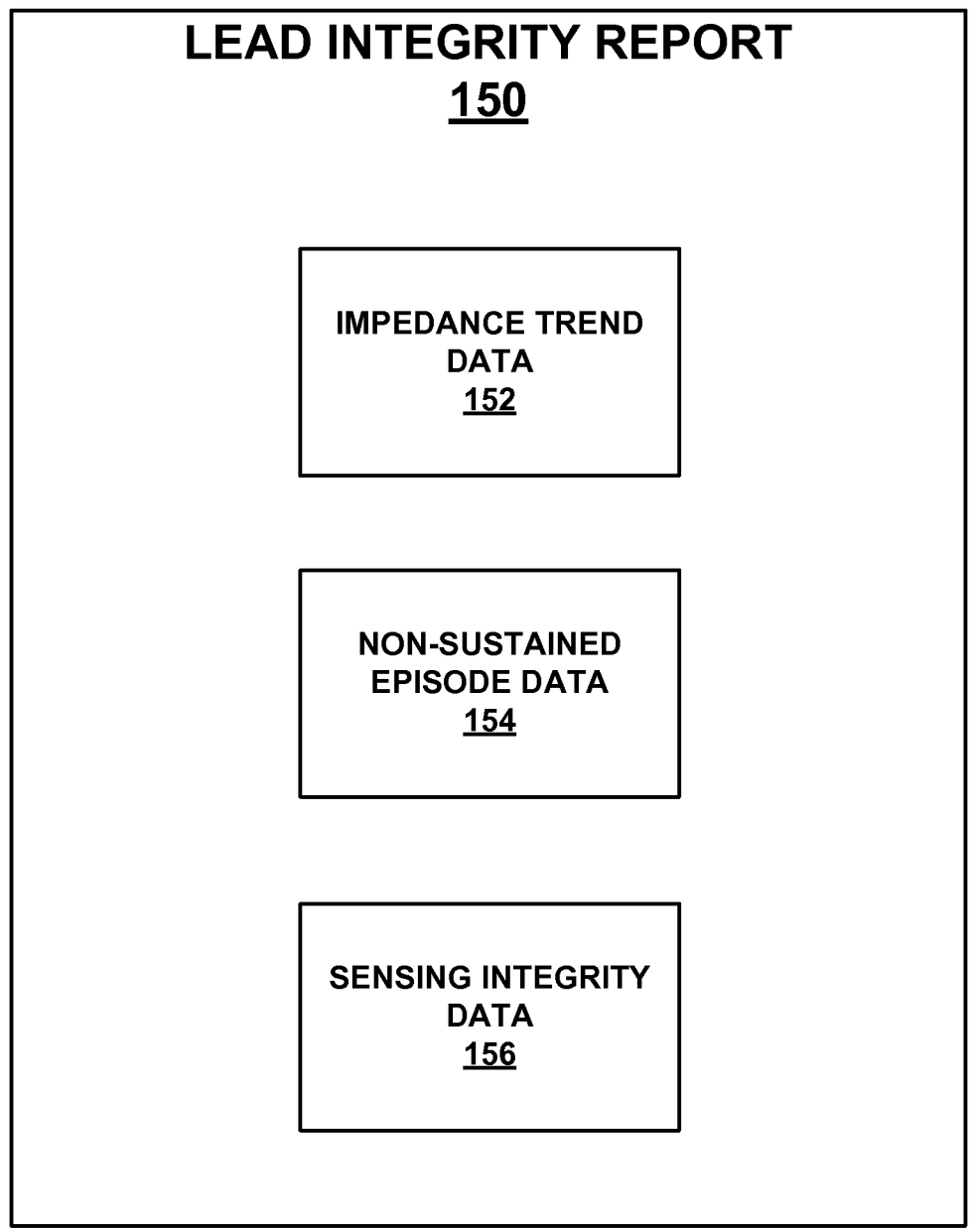
FIG. 8 is a conceptual diagram illustrating details of a lead integrity report that includes diagnostic information associated with an electrode lead, according to one embodiment.

FIG. 8 is a conceptual diagram illustrating details of a lead integrity report 150 that includes diagnostic information associated with an electrode lead, according to one embodiment. In some cases, lead integrity report 150 may be displayed on programmer 24 (such as within user interface 104 of programmer 24) based upon diagnostic data that is provided by IMD 16. In some cases, lead integrity report 150 may be printed on a printer that is coupled to programmer 24. In certain cases, lead integrity report 150 may be provided to external device 132 (FIG. 6) via network 130. External device 132 may provide lead integrity report 150 to one or more of computing devices 134A-134N as a textual report, a report within an email message, an audible report, or as a report in another form, including an alert. As a result, lead integrity report 150 may be provided in multiple different formats to different devices. Users of computing devices 134A-134N may log into external device 132 to access lead integrity report 150, in some cases. In other cases, external device 132 may automatically provide lead integrity report 150 to one or more of computing devices 134A-134N as an alert, such as a visual or audio alert.

Lead integrity report 150 may include impedance trend data 152, non-sustained episode data 154, and sensing integrity data 156. In one embodiment, programmer 24 and/or external device 132 obtain impedance trend data 152, non-sustained episode data 154, and sensing integrity data 156 from IMD 16. Such data may be stored in different areas and in different formats within IMD 16. Programmer 24 and/or external device 132 combines and includes the obtained data within a single report (i.e., lead integrity report 150).

Impedance trend data 152 may include data associated with impedance measurements and trends with respect to one or more of electrode leads 18, 20, or 22 (FIG. 2). Impedance data may be obtained for different sets of electrodes. For example, impedance data may be measured across two electrodes associated with any given lead, such as between electrodes 40 and 42 of lead 18, or between electrode 40 and housing electrode 58. In many cases, IMD 16 stores impedance measurement data, and at least a portion of this data may be included within impedance trend data 152. Often, lead impedance data will be measured and stored by IMD 16 at regular intervals, such as on an hourly, daily, or weekly basis. In some cases, lead impedance data may be measured based on other evidence of oversensing that may be indicated by sensing integrity data 156. Thus, in certain cases, impedance trend data may be provided, which may show a variation of impedance data over time.

Non-sustained episode data 154 and sensing integrity data 156 include data that may relate to oversensing of IMD 16. Non-sustained episode data 154 includes data for non-sustained episodes, such as non-sustained ventricular tachycardia episodes, that are identified and stored by IMD 16. Non-sustained ventricular tachycardia (VT) episodes may be identified and stored within a non-sustained episode log in IMD 16 when a defined minimum number of events (e.g., five intervals) associated with a potential VT are detected, but not a sufficient number (e.g., sixteen intervals for detection) to indicate an occurrence of a detected, sustained VT. As an example, oversensing may last for seven beats and be classified as a non-sustained VT because it was greater than the minimum number of intervals (e.g., five intervals) to be considered a non-sustained VT, but less than the number of intervals (e.g., sixteen intervals) for detecting and treating a sustained VT.

Non-sustained VT events having average cycle lengths that are less than a predetermined threshold may be due to oversensing within IMD 16. For example, ventricular arrhythmia episodes typically have an average cycle length (i.e, average length between episodes) greater than 200 ms; thus, non-sustained episodes with average cycle lengths less than 200 ms would likely be due to oversensing. Various different thresholds may be used or contemplated. The non-sustained episode log in IMD 16 may store information relating to the non-sustained events, including a date/time stamp and an average cycle length of each non-sustained episode.

Sensing integrity data 156 includes data for a sensing integrity counter that is stored by IMD 16. This counter within IMD 16 is capable of maintaining a cumulative count of the number of very short ventricular sensed intervals, or RR intervals. Often, sensing integrity data 156 is maintained and stored after the cumulative count exceeds a predetermined threshold, because this data may be indicative of oversensing. For example, a small number of very short ventricular sensed intervals may be expected in some cases. However, a condition of oversensing may be present if the cumulative count exceeds a predetermined threshold. In these cases, IMD 16 may store and maintain sensing integrity data 156 for subsequently sensed very short ventricular intervals.

By displaying the impedance trend data 152, non-sustained episode data 154, and sensing integrity data 156 within a single lead integrity report 150, both impedance and other forms of diagnostic data are made available to a clinician to help diagnose a possible lead condition. Various information associated with lead integrity may be combined into one report, which may help reduce the time that the clinician spends reviewing data on various different screens or reports. In this manner, by combining multiple types of information, the clinician may be able to more quickly and effectively detect a lead condition, e.g., in comparison to reviewing the different types of information individually. Examples of information contained within impedance trend data 152, non-sustained episode data 154, and sensing integrity data 156 are shown in FIGS. 10-14 and described in more detail below.

In one embodiment, impedance trend data 152, non-sustained episode data 154, and sensing integrity data 156 may include data for a shared point in time or time interval, such that a clinician may review multiple forms of diagnostic data for a lead from this shared point in time or time interval (e.g., hour, day, week, month). In this embodiment, impedance trend data 152 for at least one point in time may be displayed within a first display area, such as within a first display area in user interface 104 of programmer 24. Additional diagnostic data, such as non-sustained episode data 154 and/or sensing integrity data 156, may be concurrently displayed for at least one point in time within one or more other display areas. Generally speaking, a display area may be any portion of a screen and/or window for displaying data. By viewing the combined information that is displayed in these various display areas, a clinician is able to quickly review diagnostic data for the lead (and/or electrical paths associated with the lead) for the at least one shared point in time, and may be able to more quickly draw a conclusion concerning the condition of the lead.

In one embodiment, impedance trend data 152 includes data associated with one particular lead. In another embodiment, impedance trend data 152 may include data associated with multiple leads. In this embodiment, the data associated with each of these multiple leads may be included within lead integrity report 150. In one embodiment, non-sustained episode data 154 and sensing integrity data 156 includes data associated with one or more leads.

Figure 9:
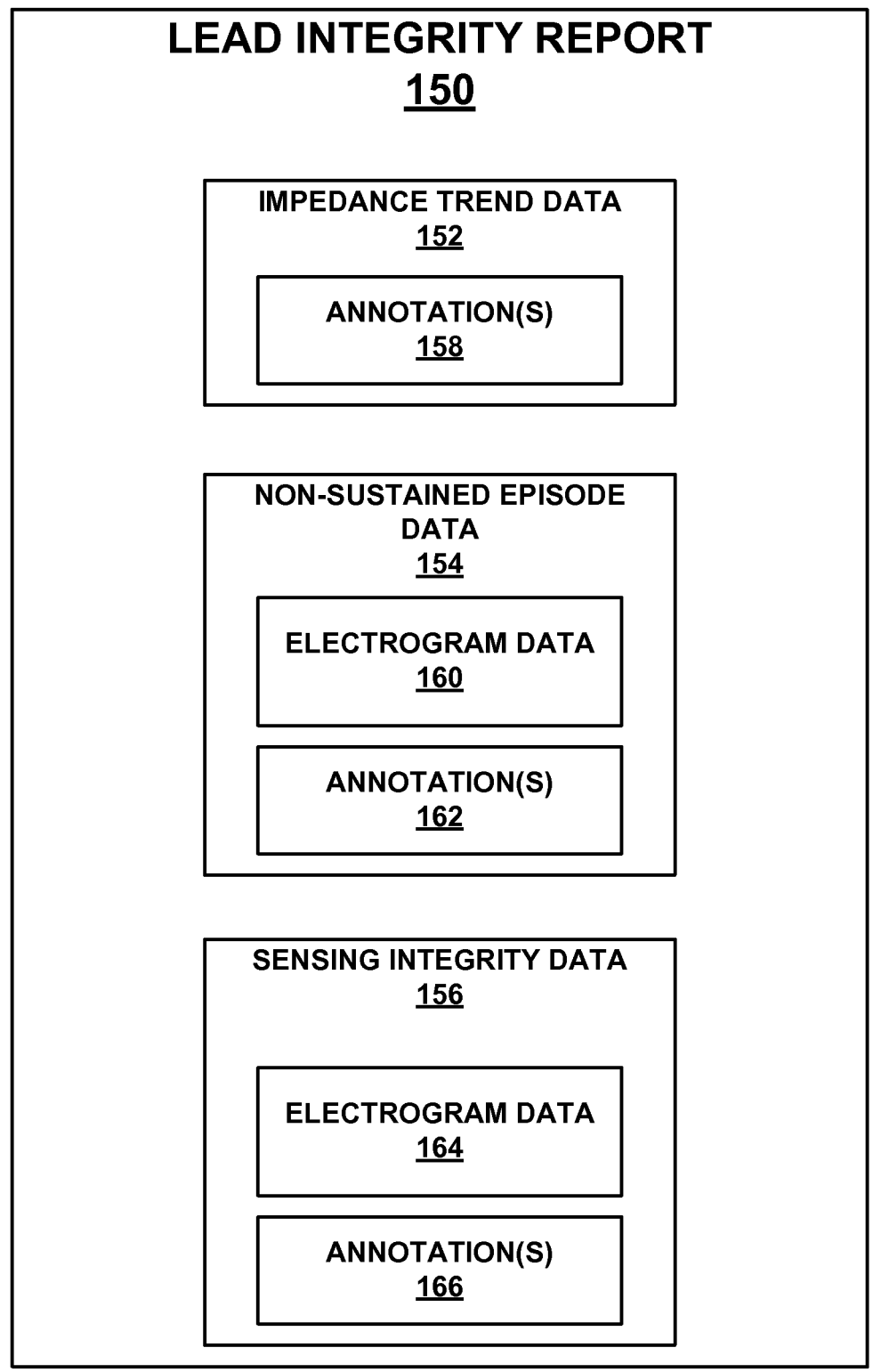
FIG. 9 is a conceptual diagram illustrating additional details of the lead integrity report shown in FIG. 8, according to one embodiment.

FIG. 9 is a conceptual diagram illustrating additional details of the lead integrity report 150 shown in FIG. 8, according to one embodiment. In this embodiment, one or more annotations are included within lead integrity report 150. For example, impedance trend data 152 includes one or more annotations 158. These annotations 158 may comprise visual annotations that are automatically provided, or identified, within impedance trend data 152, and they may also be based upon, or provided by, user input (e.g., clinician input). For example, programmer 24 may automatically provide one or more of annotations 158 by identifying outliers, or statistical deviants, within the impedance trend data 152. A clinician may also identify outliers or other anomalies within the impedance trend data 152 as one or more of the annotations 158. In general, annotations 158 may include visual annotations, such as textual annotations, comments, boxes, highlighted information, different fonts, italicized fonts, underlined text, blinking text, boxed text, colored text, icons, symbols, or other forms of visual annotation. In some cases, annotations 158 may include audio annotations, such as sounds, voice recordings, or other audio signals that identify certain data elements or identify certain alerts or audible indications. In some cases, one or more of annotations 158 may be automatically provided by annotation module 148 (FIG. 7) to identify potentially relevant or important portions of impedance trend data 152, as determined by analysis module 144.

Non-sustained episode data 154 may also include one or more visual and/or audio annotations 162. For example, annotations 162 may include identifiers of particular or noteworthy non-sustained episodes within a series of episodes. Annotations 162 may be automatically provided, or identified, within non-sustained episode data 154, and they may also be based upon, or provided by, user input (e.g., clinician input). Non-sustained episode data 154 may also include electrogram data 160, such as one or more electrogram strips. Electrogram data 160 may be stored within IMD 16. In certain cases, electrogram data 160 may include an electrogram strip for one or more non-sustained episodes within non-sustained episode data 154, as will be described in more detail below. Annotations of electrogram data 160 may indicate where oversensed event have occurred. In some cases, one or more of annotations 162 may be automatically provided by annotation module 148 (FIG. 7) to identify potentially relevant or important portions of non-sustained episode data 154, as determined by analysis module 144.

Figure 10:
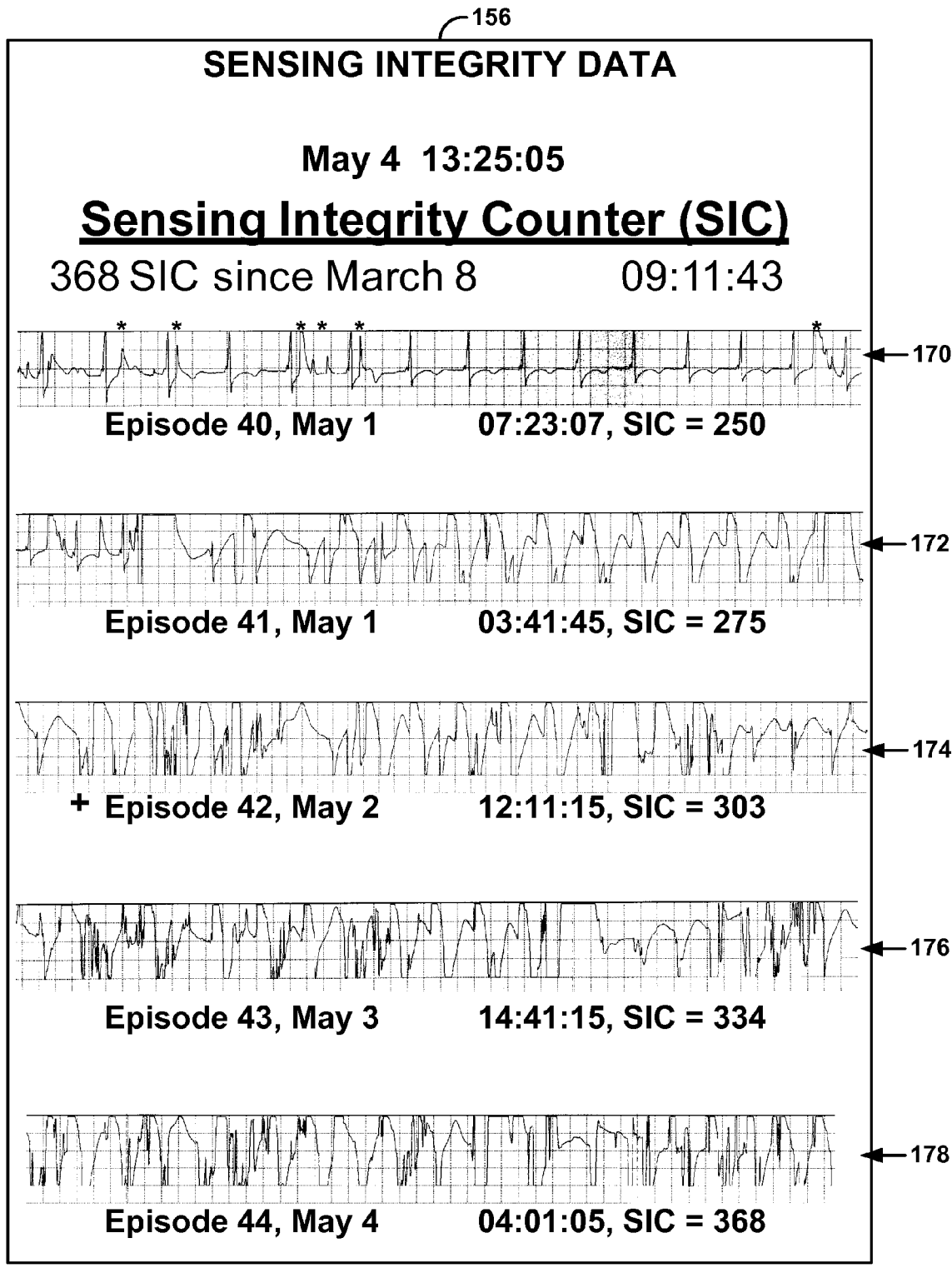
FIG. 10 is a visual diagram illustrating an example of sensing integrity counter data that may be displayed within the lead integrity report of FIG. 8.

Sensing integrity data 156 may include one or more visual and/or audio annotations 166. For example, annotations 166 may include identifiers or comments for particular or noteworthy episodes associated with certain counts within the sensing integrity data 156. Annotations 166 may be automatically provided, or identified, within impedance trend data 152, and they may also be based upon, or provided by, user input (e.g., clinician input). Sensing integrity data 156 may also include electrogram data 164, such as one or more electrogram strips. In certain cases, electrogram data 164 may include an electrogram strip for each episode that is associated with a certain count within the sensing integrity data 156, as shown in FIG. 10. In some cases, one or more of annotations 166 may be automatically provided by annotation module 148 (FIG. 7) to identify potentially relevant or important portions of sensing integrity data 156, as determined by analysis module 144.

FIG. 10 is a visual diagram illustrating an example of sensing integrity data 156 that may be displayed within the lead integrity report 150 of FIG. 8. In this example, it is assumed that IMD 16 maintains and stores sensing integrity data 156, which may then be included within lead integrity report 150. FIG. 10 shows that sensing integrity data 156 includes three hundred and sixty eight events since March 8 (in this example). Each of these events corresponds to a count of very short ventricular sensed intervals, or R-R intervals, which, over time, may be indicative of oversensing. A SIC (sensing integrity counter), which is part of sensing integrity data 156, maintains a cumulative count of these episodes. Thus, in some cases, sensing integrity data 156 may include trend information for the cumulative count of episodes over time.

As is shown in FIG. 10, sensing integrity data 156 also includes stored electrogram data strips. These stored electrogram data strips are part of electrogram data 164, and may provide snapshots of electrogram data for lead 18, 20, and/or 22 at periodic points in time. The electrogram data 164 is associated with one or more values of the SIC counter. In certain cases, specific episode and/or electrogram data strips may be stored and maintained by IMD 16 after the SIC counter reaches or exceeds a predetermined threshold value. In the example of FIG. 10, an example threshold value may be two hundred and fifty. FIG. 10 shows that, when the SIC counter reaches a value of two hundred and fifty for a given episode, information and electrogram data strip 170 associated with this episode and SIC value are stored and included within sensing integrity data 156. Electrogram data strip 170 provides a snapshot of the electrogram data at the time of this particular episode, which is labeled "Episode 40" and which occurred on May $1^{st}$.

IMD 16 may then continually or periodically store data within sensing integrity data 156 after the SIC counter has reached the threshold value of two hundred and fifty. In some cases, IMD 16 may store data within sensing integrity data 156 for every episode after the value of the SIC counter has reached the threshold value, but because this may require a larger amount of memory storage, IMD 16 will typically only store data on a periodic basis, such as in the example shown in FIG. 10. FIG. 10 shows that episode data within sensing integrity data 156 has been captured and stored for four additional episodes, labeled "Episode 41," "Episode 42," "Episode 43," and "Episode 44."

Electrogram data strip 172 is associated with "Episode 41," which also occurred on May $1^{st}$ when the SIC counter accumulated a value of two hundred and seventy five. Electrogram data strip 174 is associated with "Episode 42," which occurred on May $2^{nd}$ when the SIC counter accumulated a value of three hundred and three. Electrogram data strip 176 is associated with "Episode 43," which occurred on May $3^{rd}$ when the SIC counter accumulated a value of three hundred and thirty four. Electrogram data strip 178 is associated with "Episode 44," which occurred on May $4^{th}$ when the SIC counter accumulated a value of three hundred and sixty eight. Data strips 170, 172, 174, 176, and 178 are part of electrogram data 164 shown in FIG. 9. A clinician may review the sensing integrity data 156 to identify potential unhealthy trends, electrogram data, or regular SIC count data that exceeds the threshold to identify potential oversensing conditions.

In some cases, annotations may be provided within sensing integrity data 156, either automatically or by way of user input. For example, in FIG. 10, a clinician may insert an annotation ("+" sign) next to a particular, noteworthy event or episode, such as "Episode 42." The clinician may wish the highlight this particular episode for purposes of lead or device diagnosis, or highlight the corresponding data strip 174.

In some cases, one or more of the data strips, such as data strips 170, 172, 174, 176, and/or 178, may include annotations indicating where oversensed events may have occurred. For example, in data strip 170 in FIG. 10, multiple asterisks ("*") are shown as annotations to indicate the points where oversensing has occurred during "Episode 40." Multiple forms of annotations may be used, and multiple data strips may include such annotations.

FIG. 11 is a visual diagram illustrating an example of non-sustained episode data 154 that may be displayed within the lead integrity report 150 of FIG. 8. In the example of FIG. 11, IMD 16 captures and stores non-sustained (NST) episodes that satisfy a predetermined condition, such as those episodes having a ventricular cycle length below a predetermined threshold of 200 ms. Ventricular arrhythmia episodes typically have an average cycle length greater than 200 ms. Thus, non-sustained episodes with cycle lengths less than 200 ms may be caused by oversensing, and may potentially indicate a lead condition.

FIG. 11 shows that, in the example, twenty out of fifty (or 40%) of the non-sustained episodes have a ventricular cycle length less than 200 ms. Some of these episodes, having identifiers of "81" through "84", "87," and "89," are shown in FIG. 11. Each recorded non-sustained episode has an identifier, a date/time, an atrial cycle length, a ventricular cycle length, and a duration. Because 40% of the non-sustained episodes have a ventricular cycle length less than 200 ms, a clinician may determine, after reviewing non-sustained episode data 154, that there is oversensing of such non-sustained episodes with large cycle lengths.

FIG. 11 also shows an example of a visual annotation (which may be part of annotations 162). A "+" sign annotation is shown within non-sustained episode data 154, which corresponds to the episode having an identifier of "89." This is the most recent non-sustained episode that has a ventricular cycle less than 200 ms. In one scenario, a clinician may provide this annotation, and in another scenario, the annotation may automatically be provided, such as by programmer 24 when non-sustained episode data 154 is displayed by programmer 24 to the clinician.

Electrogram data strip 180, which is part of electrogram data 160 (FIG. 9), is also displayed in FIG. 11 for the most recent non-sustained episode, "89," that has a ventricular cycle length less than 200 ms. This electrogram data strip 180 is captured and stored by IMD 16, and provides the clinician with a snapshot view of the electrogram data with respect to leads 18, 20, and/or 22 around the time of this particular episode. Electrogram data strip 180 may also provide the clinician with insight as to whether there may be any irregularities.

In one scenario, electrogram data strip 180 may be automatically displayed for the most recent non-sustained episode having a ventricular cycle less than 200 ms. However, in other scenarios where non-sustained episode data 154 is displayed to a user, a user may select one of the non-sustained episodes, and then the associated electrogram data (such as electrogram data strip 180) can be displayed. In some cases, one or more of the data strips, such as data strip 180, may include annotations (e.g., asterisks) indicating where oversensed events may have occurred.

Figure 12:
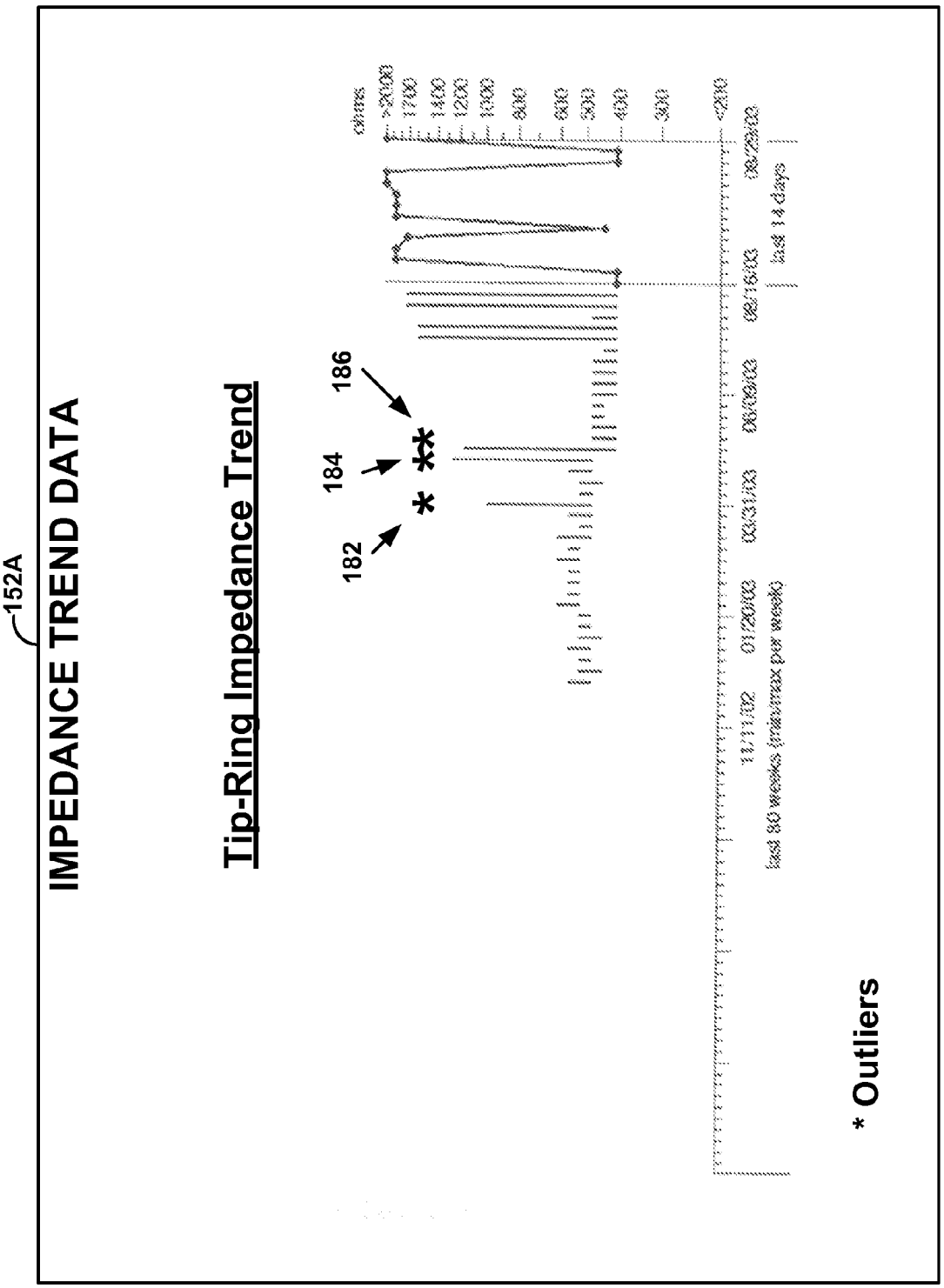
FIG. 12 is a visual diagram illustrating a first example of impedance trend data that may be displayed within the lead integrity report of FIG. 8.

FIG. 12 is a visual diagram illustrating a first example of impedance trend data 152A that may be displayed within the lead integrity report 150 of FIG. 8. Impedance trend data 152A may be part of impedance trend data 152 shown in FIG. 8. In the example of FIG. 12, impedance trend data is shown for impedance measurements made between a tip electrode (such as electrode 42 shown in FIG. 2) and a ring electrode (such as electrode 40 shown in FIG. 2) for an electrode lead. IMD 16 measures and records the impedance data that is used to generate the trend data, according to one embodiment.

In the example of FIG. 12, impedance measurement data (in ohms) is shown along the y-axis of the graph of the trend data, and time is shown along the x-axis. The graph shows impedance measurement data for both recent weeks as well as days. A clinician may review and analyze the trend shown in the graph, with respect to the impedance measurement data, to identify any abnormalities or anomalies. For example, the clinician may identify outlier impedance measurement values shown at points 182, 184, and 186 in FIG. 12. The clinician may mark points 182, 184, and 186 using one or more annotations, which may be part of annotations 158. In the example of FIG. 12, the annotations include asterisks.

In other cases, IMD 16 and/or programmer 24 may automatically identify statistical outlier impedance values and identify points 182, 184, and/or 186 shown in FIG. 12. For example, IMD 16 and/or programmer 24 may compare individual impedance measurements to predetermined thresholds, or to thresholds that may be determined relative to calculated mean impedance values, such as is described in U.S. Pat. No. 7,289,851 to Gunderson et al., which issued on Oct. 30, 2007, entitled, "Method and apparatus for identifying lead-related conditions using impedance trends and oversensing criteria," and which is incorporated herein by reference in its entirety. The clinician may determine that there is a suspected lead-related condition based upon impedance trend data 152A and the identified outlier points 182, 184, and/or 186.

Figure 13:
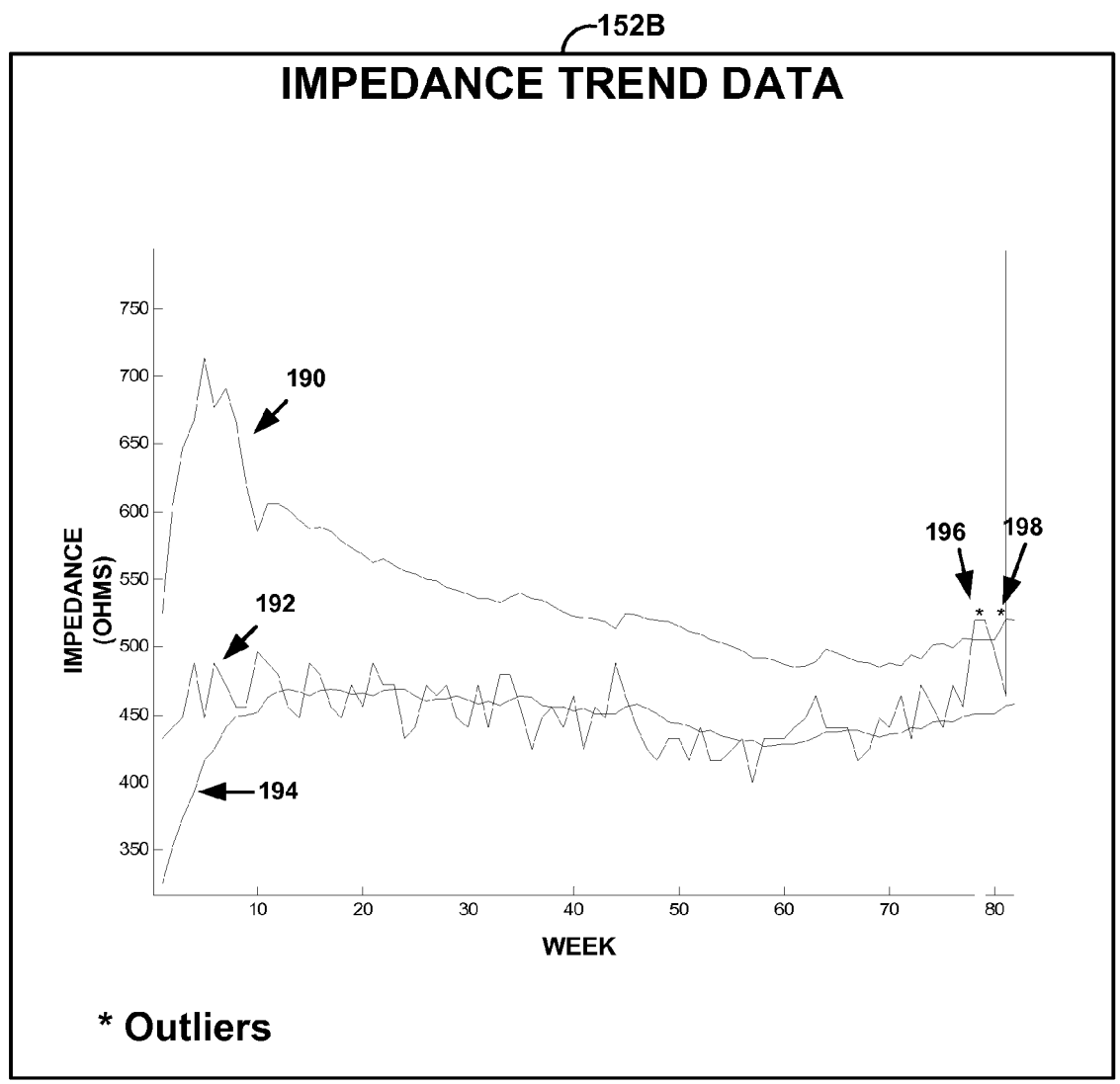
FIG. 13 is a visual diagram illustrating a second example of impedance trend data that may be displayed within the lead integrity report of FIG. 8.

FIG. 13 is a visual diagram illustrating a second example of impedance trend data 152B that may be displayed within the lead integrity report 150 of FIG. 8. Impedance trend data 152B may be part of impedance trend data 152 shown in FIG. 8. In this example, impedance trend data 152B may be associated with one particular lead. Of course, impedance trend data 152, in general, may include trend information for multiple leads (and electrode combinations), and graph data, such as the data shown in FIG. 13, may be shown for each of these multiple leads. This data may be shown in one or more reports, and may be shown in one or more screen displays (e.g., on the same or different screens). A clinician may be able to view the trend data associated with each of the multiple leads, and may even be displayed with annotations, or in a prioritized fashion, based upon the number of conditions that may have been identified for each lead, to help identify for the clinician particular leads that may have lead-related conditions.

In the example of FIG. 13, impedance measurement data (in ohms) is shown along the y-axis of the graph of the trend data, and time, in weeks, is shown along the x-axis. In the graph, weekly measured maximum impedance values are shown in curve 192, mean values of the weekly maximum impedance values are shown in curve 194, and the weekly upper limits of the expected maximum impedance values are in curve 190. An upper limit, or threshold, for a given week may be determined by the mean value plus a variability factor that is determined by the estimated variability.

Typically, during the first few weeks of measurement, the variability factor may be adapted and adjusted to the conditions within patient 14. The variability factor is a mean value that may be continually adjusted in each of the first few weeks, according to one embodiment. In FIG. 13, curve 190 has been substantially adapted, or adjusted, by week ten, in this example. Prior to week ten, which may be referred to as an initialization stage, the initial mean and variability values are being determined and adjusted, according to one embodiment.

Changes in the weekly values of measured maximum impedance values, shown in curve 192, and particularly larger changes, may be indicative of potential conditions of the lead, as opposed to variability within the lead based upon the condition of the patient 14. Sometime during week eighty one in the example of FIG. 13, the maximum impedance exceeds 10000 ohms. Curve 192 intersects curve 190 prior to this significant change. Point 198 may therefore be identified as a statistical outlier (where the value of curve 192 exceeds the value of 190 at that point in time.)

However, the maximum impedance values in weeks seventy eight and seventy nine are unexpected, giving the potential for early indication of a potential condition. During these weeks, the values of curve 192 exceed the values of curve 190, indicating that the maximum impedance value has exceeded the threshold value that is based on the mean maximum impedance value and the mean variability value. Thus, point 196 may be identified as a statistical outlier with respect to these weeks.

A clinician may review and analyze the trend shown in the graph of FIG. 13, with respect to the mean impedance measurement data, to identify any abnormalities or anomalies. For example, the clinician may identify outlier impedance measurement values shown at points 196 and 198 using one or more annotations, which may be part of annotations 158. In other cases, IMD 16 and/or programmer 24 may automatically identify statistical outlier impedance values and identify points 196 and 198 based upon the measured impedance values and the calculated mean and variability values. In this example, points 196 and 198 may comprise annotations that are visually represented as asterisks.

By displaying the impedance trend data 152, non-sustained episode data 154, and sensing integrity data 156 within a single lead integrity report 150, impedance and other forms of diagnostic data are made available for a clinician in a consolidated report to help diagnose a possible lead-related condition. In certain cases, the clinician may want to review each of impedance trend data 152, non-sustained episode data 154, and sensing integrity data 156 before making any conclusions regarding the integrity of one or more leads, such as leads 18, 20, or 22. In some cases, impedance data for a given lean, by itself, may not provide sufficient information to diagnose a potential condition. In these cases, the clinician may want to assess the possibility or trend of event or episode oversensing, as indicated in non-sustained episode data 154 and/or sensing integrity data 156, in addition to analyzing the impedance trend data 152, before making a diagnosis for one or more of leads 18, 20, or 22. By providing all of this data within a single report 150, and by also providing annotations in certain cases to highlight items or points, a clinician is able to more quickly and effectively make diagnoses about the condition or integrity of leads 18, 20, and 22 that are coupled to IMD 16.

Figure 14:
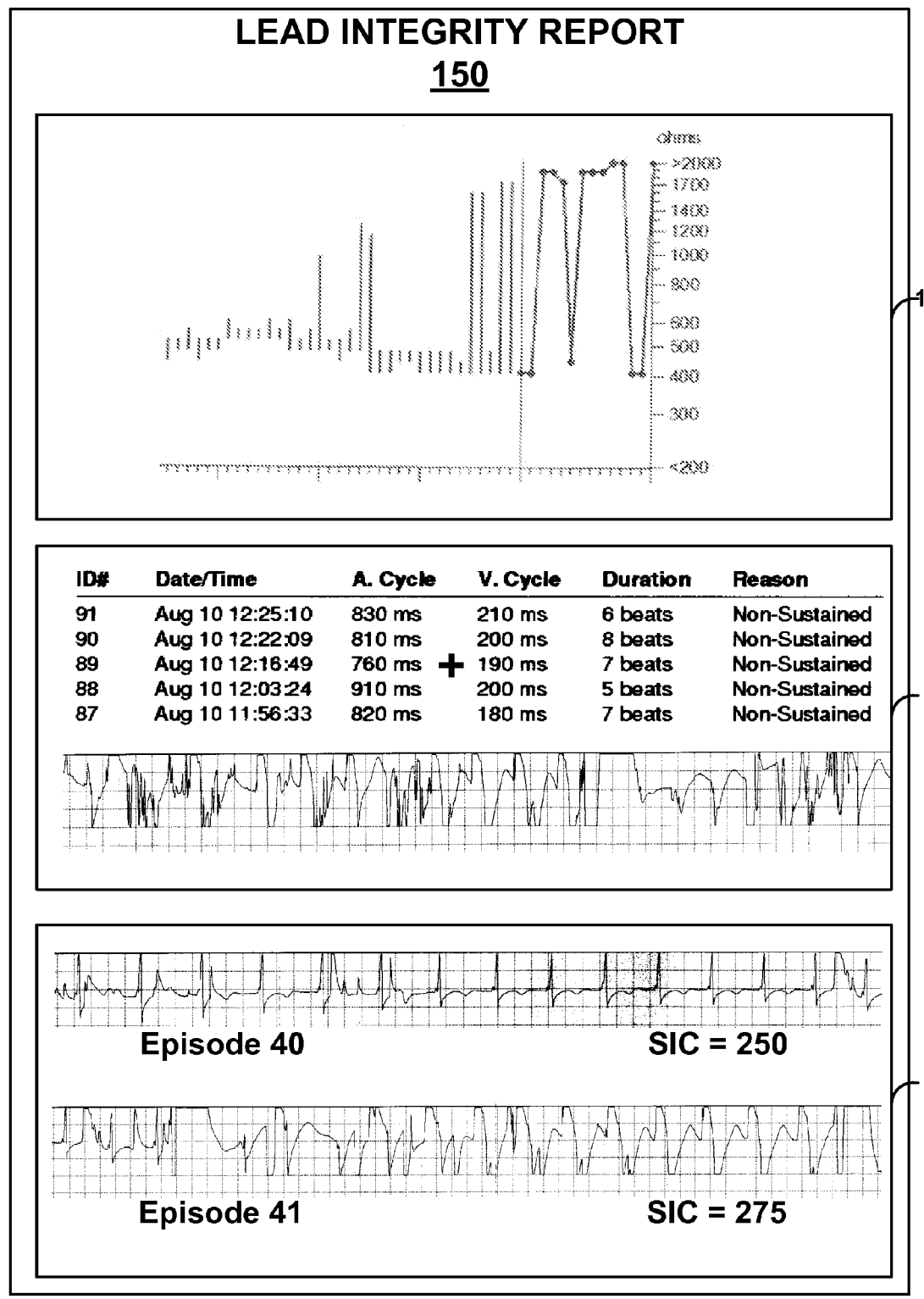
FIG. 14 is a visual diagram illustrating an example of impedance trend data, non-sustained episode data, and sensing integrity data as included within a lead integrity report.

FIG. 14 is a visual diagram illustrating an example of impedance trend data 152A, non-sustained episode data 154, and sensing integrity data 156 as included within lead integrity report 150. As is shown in FIG. 14, lead integrity report 150 includes each of impedance trend data 152A, non-sustained episode data 154, and sensing integrity data 156 in one single report that may be reviewed or annotated by a clinician. The clinician may be able to more efficiently and/or effectively identify possible or suspected lead-related conditions by reviewing various different forms, or types, of diagnostic information in one report. In some cases, impedance trend data 152A, non-sustained episode data 154, and sensing integrity data 156 may be displayed within lead integrity report 150 for a given period of time, or time interval (e.g., hours, days, weeks), such that the clinician may be able to compare the different types of diagnostic data for a share timed period. In these cases, a date or other time period may be displayed along a horizontal (x-axis), and there may be one or more annotations provided for impedance trend data 152A indicating where particular non-sustained episodes may have occurred, and/or indicating when a counter for sensing integrity data 156 reached one or more thresholds. In some cases, a timeline may be provided to display identified non-sustained episode data 154 and/or sensing integrity data 156 that may cross one or more thresholds. A user may then graphically indicate or select any points on the timeline for the identified data to retrieve or view electrograms for those points in time.

Figure 15:
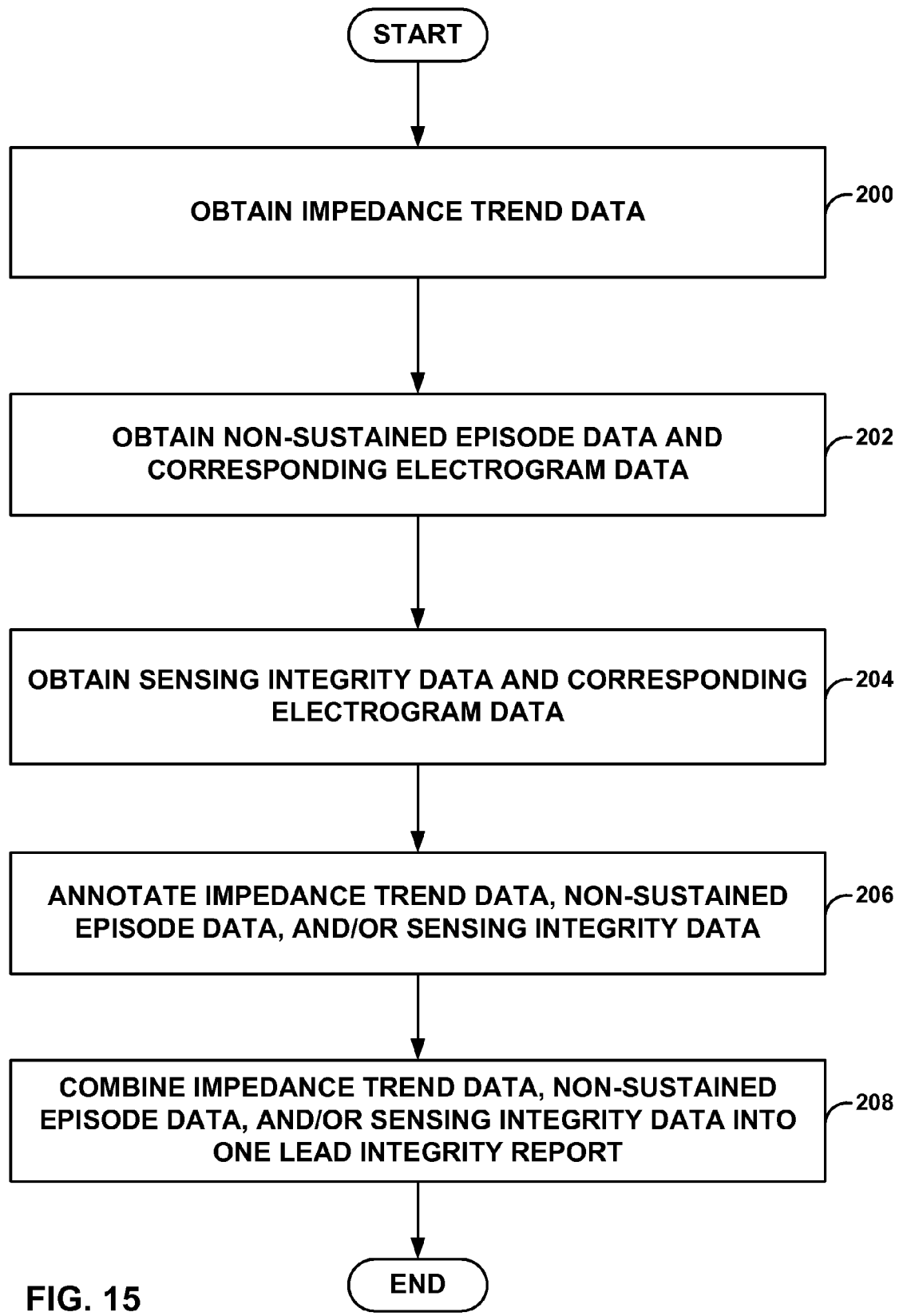
FIGS. 15 and 16 are flow diagrams illustrating example methods that may be performed by an implantable medical device and/or a programmer, according to one embodiment.
Figure 16:
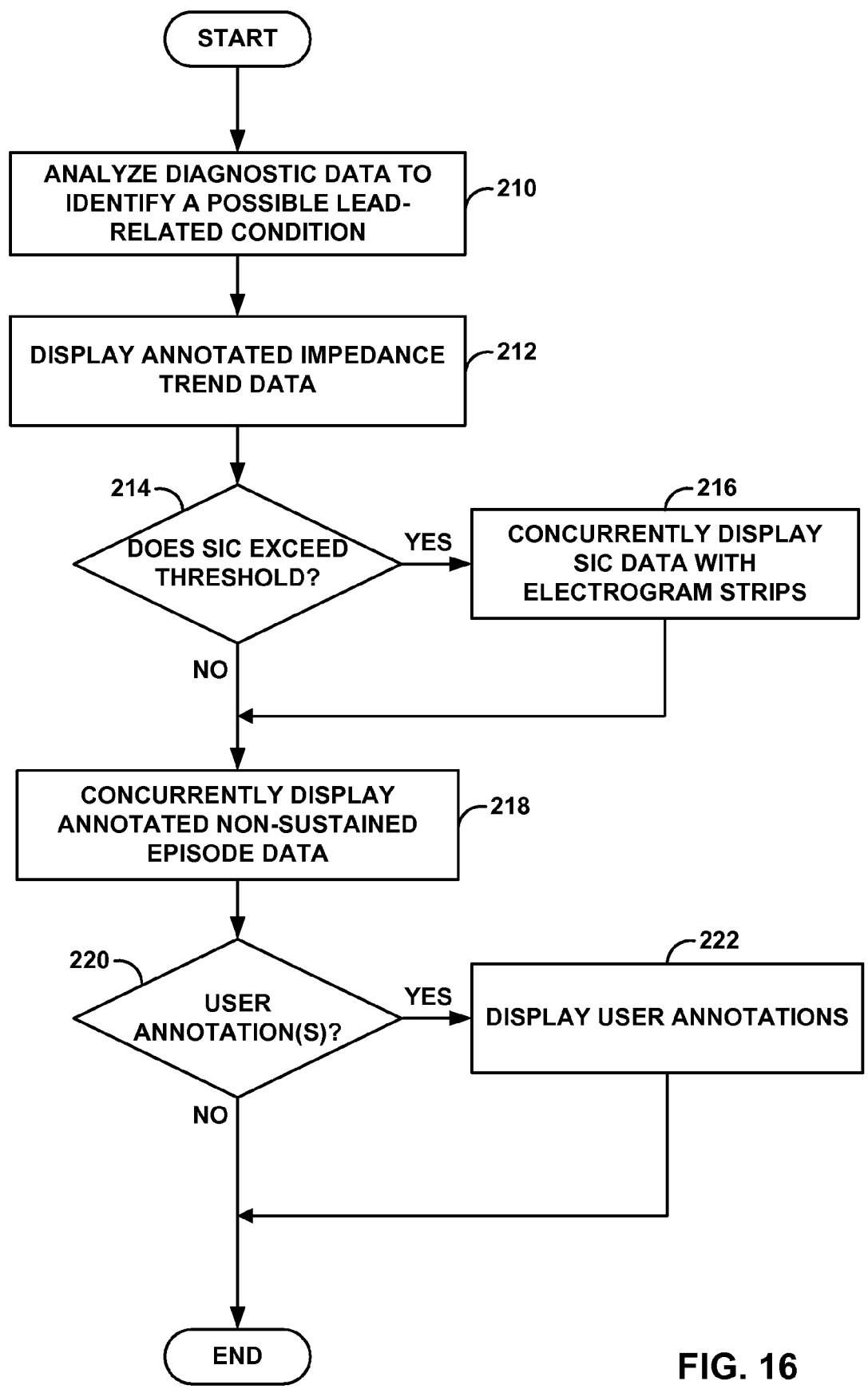

FIGS. 15 and 16 are flow diagrams illustrating example methods that may be performed by IMD 16, programmer 24, and/or external device 132, according to one embodiment. For purposes of illustration only, it will be assumed in the subsequent description that these example methods are performed by programmer 24.

At 200, programmer 24 obtains impedance trend data 152 (FIG. 8), which has been measured for one or more electrical paths associated with an implantable electrode lead, such as lead 20, 22, or 24. For example, programmer 24 may obtain impedance trend data 152 from IMD 16. Each electrical path may include a plurality of electrodes associated with lead 20, 22, or 24.

At 202, programmer 24 obtains non-sustained episode data 154 and corresponding electrogram data 160 (FIG. 9). In some cases, the electrogram data 160 may include one or more electrogram data strips, such as data strip 180 shown in FIG. 11. Programmer 24 may obtain non-sustained episode data 154 and corresponding electrogram data 160 from IMD 16. In some cases, the electrogram data 160 may be associated with at least one non-sustained episode within non-sustained episode data 154 that satisfies a predetermined condition (such as, for example, episodes having a cycle length that is less than a defined threshold).

At 204, programmer 24 obtains sensing integrity data 156 and corresponding electrogram data 164. In one embodiment, electrogram data 164 is associated with at least one value of a sensing integrity counter, which is part of sensing integrity data 156. In some cases, the electrogram data 164 may include one or more electrogram data strips, such as data strips 170, 172, 174, 176, and 178 shown in FIG. 10, where one data strip is associated with each of a plurality of values of the sensing integrity counter that exceeds a predetermined threshold. Programmer 24 may obtain sensing integrity data 156 and corresponding electrogram data 164 from IMD 16. In one embodiment, non-sustained episode data 154 and sensing integrity data 156 comprise additional diagnostic data, distinct from impedance trend data 152, for the electrode lead (such as lead 18, 20, or 22).

At 206, programmer 24 may annotate one or more of the impedance trend data 152, non-sustained episode data 154, or sensing integrity data 156, either automatically or in response to received user input that specifies one or more annotations. The annotations may include annotations 158, 162, and/or 166 (FIG. 9). In many cases, the annotations may comprise visual or graphical annotations, such as textual notes, comments, boxes, or highlights, for example. In certain cases, the annotations may comprise audio annotations, as described previously. The annotations may identify potentially relevant and/or important elements in the impedance trend data 152, non-sustained episode data 154, and/or sensing integrity data 156. In some cases, certain annotations may be automatically provided by annotation module 148 (FIG. 7) based upon information provided by analysis module 144.

At 208, programmer 24 combines both impedance trend data 152 and the additional diagnostic data (non-sustained episode data 154 and/or sensing integrity data 156) into a lead integrity report 150, which may indicate whether there is a potential lead-related condition. In some cases, the lead integrity report 150 may identify a condition with an electrical path and/or the electrode lead. The lead integrity report 150 may comprise a displayable report that is displayed within the user interface device 104 of programmer 24. In certain cases, the report 150 may be displayed after programmer 24 has analyzed impedance trend data 152, non-sustained episode data 154, and/or sensing integrity data 156 to identify a potential lead-related condition. In these cases, report 150 may comprise an active alert that is presented to a user, such as a clinician.

In one embodiment, displaying lead integrity report 150 includes displaying impedance trend data 152 for at least one point in time within a display area, and concurrently displaying additional diagnostic data, such as non-sustained episode data 154 and/or sensing integrity data 156, for the at least one point in time within one or more additional display areas. In this embodiment, a clinician may be able to simultaneously view multiple forms of diagnostic data for a shared point in time, or a shared time interval.

FIG. 16 is a flow diagram illustrating another example method that may be performed by IMD 16, programmer 24, and/or external device 132, according to one embodiment. For purposes of illustration only, it will be assumed in the subsequent description that this example method is performed by programmer 24.

At 210, programmer 24 analyzes diagnostic data to identify a possible lead-related condition, such as a condition of lead 18, 20, or 22. Programmer 24 may receive the diagnostic data from IMD 16, and the diagnostic data may include impedance trend data 152, non-sustained episode data 154, and/or sensing integrity data 156.

At 212, programmer 24 displays annotated impedance trend data, which may include one or more of annotations 158 (FIG. 9) to impedance trend data 152, based upon the analysis. The annotations 158 may be automatically generated by programmer 24 or may be specified by user input. Certain of the annotations 158 may identify or highlight certain relevant and/or otherwise important elements within the impedance trend data 152, such as impedance measurements that are statistical outliers. Based upon its analysis of the data, programmer 24 may also determine which portions of impedance trend data 152 are to be displayed or included within a report.

At 214, programmer 24 determines whether a value of a sensing integrity counter (SIC), which is part of sensing integrity data 156, exceeds a predefined threshold. The value of the SIC may identify a cumulative count of short-sensed intervals, such as short ventricular R-R intervals).

If the SIC counter does not exceed the threshold, programmer 24 concurrently displays annotated non-sustained episode data at 218, which may include one or more annotations 162 to non-sustained episode data 154. The annotations 162 may be automatically generated by programmer 24 or may be specified by user input. Certain of the annotations 162 may identify or highlight certain relevant and/or otherwise important elements within the non-sustained episode data 154. Based upon its analysis of the data, programmer 24 may also determine which portions of non-sustained episode data 154 are to be displayed or included within a report.

If, however, the SIC counter does exceed the threshold, programmer 24 also concurrently displays SIC data, which may be part of sensing integrity data 156, along with electrogram strip data at 216. The electrogram strip data may be part of electrogram data 164. The electrogram strip data may include electrogram strips that are each associated with at least one value of the SIC counter. In some cases, programmer 24 may also provide one or more annotations to the sensing integrity data 156, which may be automatically generated by programmer 24 or specified by user input. Certain ones of these annotations may identify or highlight certain relevant and/or otherwise important elements within the sensing integrity data 156. Based upon its analysis of the data, programmer 24 may also determine which portions of sensing integrity data 156 are to be displayed or included within a report.

At 220, programmer 24 determines if there are any user-based annotations at 220. A user, such as a clinician, may specify one or more of such annotations. If there are any such user-based annotations to process, such as by receiving user-based input via user interface 104 of programmer 24, programmer 24 displays the requested user annotations within user interface 104 at 22 in FIG. 16. These annotations may be part of annotations 158, 162, and/or 166 shown in FIG. 9 (to impedance trend data 152, non-sustained episode data 154, and/or sensing integrity data 156, respectively).

The techniques described in this disclosure, including those attributed to IMD 16, programmer 24, external device 132, or various constituent components, may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure.

Various embodiments of the disclosure have been described. For example, although many of the techniques that are described relate to cardiac therapy, these and other techniques could be applied to other therapies in which lead integrity may be important or relevant, such as, for example, spinal cord stimulation, deep brain stimulation, pelvic floor stimulation, gastric stimulation, occipital stimulation, or functional electrical stimulation. Thus, the various embodiments described herein, as well as other embodiments, are within the scope of the following claims.

The invention claimed is:

1. A method comprising:
   obtaining, by a device, impedance trend data for an electrical path, the electrical path comprising a plurality of electrodes;
   obtaining, by the device, additional diagnostic data that is associated with the electrical path, the additional diagnostic data being distinct from the impedance trend data;
   combining, by the device, both the impedance trend data and the additional diagnostic data into a displayable report that indicates whether there is a possible condition with the electrical path, wherein the impedance trend data for at least one point in time is displayable within a first display area of the displayable report, and wherein the additional diagnostic data for the at least one point in time is concurrently displayable within a second display area of the displayable report; and
   generating for display, by the device, the displayable report, wherein the displayable report includes:
      the impedance trend data and the additional diagnostic data, and
      visual annotations that each separately annotate at least one of the impedance trend data or the additional diagnostic data to indicate a possible abnormality in the at least one of the impedance trend data or the additional diagnostic data.

2. The method of claim 1, wherein at least one of the plurality of electrodes is located on an implantable medical lead coupled to an implantable medical device.

3. The method of claim 1, further comprising:
   analyzing one or more of the impedance trend data and the additional diagnostic data to identify the possible condition with the electrode lead.

4. The method of claim 1, further comprising:
   displaying the displayable report.

5. The method of claim 1, wherein visually annotating the displayable report comprises receiving user input to specify the annotations.

6. The method of claim 1, wherein obtaining the additional diagnostic data comprises obtaining non-sustained episode data.

7. The method of claim 6, wherein obtaining the non-sustained episode data comprises obtaining electrogram data associated with at least one non-sustained episode within the non-sustained episode data that satisfies a predetermined condition.

8. The method of claim 7, further comprising:
   visually annotating the electrogram data associated with the at least one non-sustained episode to identify at least one occurrence of oversensing.

9. The method of claim 7, wherein the at least one non-sustained episode comprises a non-sustained ventricular tachycardia event.

10. The method of claim 6, wherein obtaining the additional diagnostic data further comprises obtaining sensing integrity data for a sensing integrity counter that identifies a count of short-sensed intervals.

11. The method of claim 10, wherein obtaining the sensing integrity data comprises obtaining electrogram data associated with at least one value of the sensing integrity counter.

12. The method of claim 11, further comprising:
   visually annotating the electrogram data associated with the at least one value of the sensing integrity counter to identify at least one occurrence of oversensing.

13. The method of claim 11, further comprising:
   storing the electrogram data associated with the at least one value of the sensing integrity counter when the count of short-sensed intervals exceeds a predetermined threshold.

14. The method of claim 13, wherein storing the electrogram data associated with the at least one value of the sensing integrity counter comprises storing an electrogram data strip for each of a plurality of values of the sensing integrity counter.

15. The method of claim 1, wherein the displayable report comprises an alert.

16. The method of claim 1, wherein generating for display the visual annotations in the displayable report to indicate the possible abnormality in at least one of the impedance trend data and the additional diagnostic data further comprises:
   identifying, by the device, the possible abnormality in at least one of the impedance trend data and the additional diagnostic data;
   in response to identifying the possible abnormality, determining, by the device, a portion of the at least one of the impedance trend data and the additional diagnostic data that includes the possible abnormality; and
   generating for display, by the device, the portion of the at least one of the impedance trend data and the additional diagnostic data that includes the possible abnormality.

17. The method of claim 1, wherein the possible abnormality comprises a statistical outlier in at least one of the impedance trend data and the additional diagnostic data.

18. A non-transitory computer-readable medium comprising instructions for causing one or more processors to:
   obtain impedance trend data for an electrical path, the electrical path comprising a plurality of electrodes;
   obtain additional diagnostic data that is associated with the electrical path, the additional diagnostic data being distinct from the impedance trend data;
   combine both the impedance trend data and the additional diagnostic data into a displayable report that indicates whether there is a possible condition with the electrical path, wherein the impedance trend data for at least one point in time is displayable within a first display area of the displayable report, and wherein the additional diagnostic data for the at least one point in time is concurrently displayable within a second display area of the displayable report; and
   generate, for display, the displayable report, wherein the displayable report includes:
      the impedance trend data and the additional diagnostic data, and
      visual annotations that each separately annotate at least one of the impedance trend data or the additional diagnostic data to indicate a possible abnormality in the at least one of the impedance trend data or the additional diagnostic data.

19. An implantable medical device comprising:
   one or more implantable medical electrode leads including a plurality of electrodes; and
   one or more processors configured to:

obtain impedance trend data for an electrical path, the electrical path comprising at least two electrodes in the plurality of electrodes;

obtain additional diagnostic data that is associated with the electrical path, the additional diagnostic data being distinct from the impedance trend data;

combine both the impedance trend data and the additional diagnostic data into a report that indicates whether there is a possible condition with the electrical path, wherein the impedance trend data for at least one point in time is displayable within a first display area of the report, and wherein the additional diagnostic data for the at least one point in time is concurrently displayable within a second display area of the report; and generate, for display, the displayable report, wherein the displayable report includes:
the impedance trend data and the additional diagnostic data, and
visual annotations that each separately annotate at least one of the impedance trend data or the additional diagnostic data to indicate a possible abnormality in the at least one of the impedance trend data or the additional diagnostic data.

20. The implantable medical device of claim 19, further comprising a stimulation generator configured to deliver stimulation via the one or more implantable medical electrode leads.

21. The implantable medical device of claim 19, wherein the additional diagnostic data comprises non-sustained episode data.

22. The implantable medical device of claim 21, wherein the non-sustained episode data comprises electrogram data associated with at least one non-sustained episode that satisfies a predetermined condition.

23. The implantable medical device of claim 22, wherein the one or more processors are further configured to visually annotate the electrogram data associated with the at least one non-sustained episode to identify at least one occurrence of oversensing.

24. The implantable medical device of claim 21, wherein the additional diagnostic data further comprises sensing integrity data for a sensing integrity counter that identifies a count of short-sensed intervals.

25. The implantable medical device of claim 24, wherein the sensing integrity data further comprises electrogram data associated with at least one value of the sensing integrity counter.

26. The implantable medical device of claim 25, wherein the one or more processors are further configured to visually annotate the electrogram data associated with the at least one value of the sensing integrity counter to identify at least one occurrence of oversensing.

27. The implantable medical device of claim 25, wherein the one or more processors are further configured to store the electrogram data associated with the at least one value of the sensing integrity counter when the count of short-sensed intervals exceeds a predetermined threshold.

28. A device comprising:
an output device; and
one or more processors configured to:
obtain impedance trend data for an electrical path, the electrical path comprising plurality of electrodes;
obtain additional diagnostic data that is associated with the electrical path, the additional diagnostic data being distinct from the impedance trend data;

combine both the impedance trend data and the additional diagnostic data into a displayable report that indicates whether there is a possible condition with the electrical path, wherein the impedance trend data for at least one point in time is displayable within a first display area of the displayable report, and wherein the additional diagnostic data for the at least one point in time is concurrently displayable within a second display area of the displayable report; and generate, for display, the displayable report, wherein the displayable report includes:
the impedance trend data and the additional diagnostic data, and
visual annotations that each separately annotate at least one of the impedance trend data or the additional diagnostic data to indicate a possible abnormality in the at least one of the impedance trend data or the additional diagnostic data.

29. The device of claim 28, wherein the output device comprises a user interface device that is configured to display the displayable report to a user.

30. The device of claim 28, wherein visually annotating the displayable report comprises receiving user input to specify the annotations.

31. The device of claim 28, wherein the output device is configured to send the displayable report to another device.

32. The device of claim 28, further comprising:
analyzing one or more of the impedance trend data and the additional diagnostic data to identify the possible condition with the electrode lead.

33. The device of claim 28, wherein the additional diagnostic data comprises non-sustained episode data.

34. The device of claim 33, wherein the non-sustained episode data comprises electrogram data associated with at least one non-sustained episode that satisfies a predetermined condition.

35. The device of claim 34, wherein the one or more processors are further configured to visually annotate the electrogram data associated with the at least one non-sustained episode to identify at least one occurrence of oversensing.

36. The device of claim 34, wherein the at least one non-sustained episode comprises a non-sustained ventricular tachycardia event.

37. The device of claim 33, wherein the additional diagnostic data further comprises sensing integrity data for a sensing integrity counter that identifies a count of short-sensed intervals.

38. The device of claim 37, wherein the sensing integrity data further comprises electrogram data associated with at least one value of the sensing integrity counter.

39. The device of claim 38, wherein the one or more processors are further configured to visually annotate the electrogram data associated with the at least one value of the sensing integrity counter to identify at least one occurrence of oversensing.

40. The device of claim 38, wherein the one or more processors are further configured to store the electrogram data associated with the at least one value of the sensing integrity counter when the count of short-sensed intervals exceeds a predetermined threshold.

41. The device of claim 40, wherein storing the electrogram data associated with the at least one value of the sensing integrity counter comprises storing an electrogram data strip for each of a plurality of values of the sensing integrity counter.

42. The device of claim 28, wherein the displayable report comprises an alert.

43. The device of claim 28, wherein the device comprises an implantable medical device, a programmer, or an external server.

44. A system comprising:
- a data collection module configured to obtain impedance trend data for an electrical path, and to obtain additional diagnostic data that is associated with the electrical path, the additional diagnostic data being distinct from the impedance trend data,
- an analysis module configured to combine both the impedance trend data and the additional diagnostic data into a displayable report that indicates whether there is a possible condition with the electrical path, wherein the impedance trend data for at least one point in time is displayable within a first display area of the displayable report, and wherein the additional diagnostic data for the at least one point in time is concurrently displayable within a second display area of the displayable report; and
- a display module configured to generate, for display, the displayable report, wherein the displayable report includes:
  - the impedance trend data and the additional diagnostic data, and
  - visual annotations that each separately annotate at least one of the impedance trend data or the additional diagnostic data to indicate a possible abnormality in the at least one of the impedance trend data or the additional diagnostic data.

45. A system comprising:
- means for obtaining impedance trend data for an electrical path;
- means for obtaining additional diagnostic data that is associated with the electrical path, the additional diagnostic data being distinct from the impedance trend data; and
- means for combining both the impedance trend data and the additional diagnostic data into a displayable report that indicates whether there is a possible condition with the electrical path, wherein the impedance trend data for at least one point in time is displayable within a first display area of the report, and wherein the additional diagnostic data for the at least one point in time is concurrently displayable within a second display area of the report; and
- means for generating, for display, the displayable report, wherein the displayable report includes:
  - the impedance trend data and the additional diagnostic data, and
  - visual annotations that each separately annotate at least one of the impedance trend data or the additional diagnostic data to indicate a possible abnormality in the at least one of the impedance trend data or the additional diagnostic data.

* * * * *